US011110138B2

(12) United States Patent
Conrad et al.

(10) Patent No.: US 11,110,138 B2
(45) Date of Patent: Sep. 7, 2021

(54) NON-REPLICATING VIRUS-DERIVED PARTICLES AND USES THEREOF

(71) Applicant: CELVERUM INC., Ottawa (CA)

(72) Inventors: David Conrad, Ottawa (CA); Cory Batenchuk, Gatineau (CA); Fabrice Leboeuf, Gatineau (CA); John Cameron Bell, Ottawa (CA)

(73) Assignee: CELVERUM INC., Ottawa (CA)

( * ) Notice: Subject to any disclaimer, the term of this patent is extended or adjusted under 35 U.S.C. 154(b) by 0 days.

(21) Appl. No.: 14/654,259

(22) PCT Filed: Dec. 20, 2013

(86) PCT No.: PCT/CA2013/051009
§ 371 (c)(1),
(2) Date: Jun. 19, 2015

(87) PCT Pub. No.: WO2014/094182
PCT Pub. Date: Jun. 26, 2014

(65) Prior Publication Data
US 2015/0320810 A1 Nov. 12, 2015

Related U.S. Application Data

(60) Provisional application No. 61/835,310, filed on Jun. 14, 2013, provisional application No. 61/740,856, filed on Dec. 21, 2012.

(51) Int. Cl.
| | | |
|---|---|---|
| C12N 7/04 | (2006.01) | |
| C12N 7/06 | (2006.01) | |
| C07K 14/00 | (2006.01) | |
| A61K 35/766 | (2015.01) | |
| C12N 7/00 | (2006.01) | |
| A61K 45/06 | (2006.01) | |
| C07K 14/005 | (2006.01) | |
| A61P 35/02 | (2006.01) | |
| A01N 63/00 | (2020.01) | |

(52) U.S. Cl.
CPC ............ *A61K 35/766* (2013.01); *A61K 45/06* (2013.01); *A61P 35/02* (2018.01); *C07K 14/005* (2013.01); *C12N 7/00* (2013.01); *C12N 7/045* (2013.01); *C12N 7/06* (2013.01); *C12N 2760/20021* (2013.01); *C12N 2760/20032* (2013.01); *C12N 2760/20061* (2013.01); *C12N 2760/20222* (2013.01); *C12N 2760/20232* (2013.01); *C12N 2760/20261* (2013.01); *C12N 2760/20263* (2013.01)

(58) Field of Classification Search
CPC ........ A61K 35/766; A61K 45/06; C12N 7/00; C12N 7/06; C12N 7/045; A61P 35/02
See application file for complete search history.

(56) References Cited

U.S. PATENT DOCUMENTS

| | | | |
|---|---|---|---|
| 5,106,619 A | 4/1992 | Wiesehahn et al. | |
| 2002/0037543 A1 | 3/2002 | Atkins et al. | |
| 2005/0260601 A1 | 11/2005 | Whitt et al. | |
| 2006/0270017 A1* | 11/2006 | Reiter ...................... | C12N 7/00 435/235.1 |
| 2008/0159957 A1 | 7/2008 | Kavanaugh et al. | |
| 2011/0052539 A1 | 3/2011 | Stojdl et al. | |
| 2011/0223148 A1 | 9/2011 | Kaneda et al. | |
| 2013/0115243 A1* | 5/2013 | Conrad .............. | A61K 39/0011 424/204.1 |

FOREIGN PATENT DOCUMENTS

| | | |
|---|---|---|
| EP | 2039773 | 8/2007 |
| EP | 2345415 B1 | 1/2015 |
| EP | 2839837 A1 | 2/2015 |
| JP | 2006-517184 | 7/2006 |
| JP | 2010-503660 | 2/2010 |
| WO | WO-2004/030631 A2 | 4/2004 |
| WO | WO-2010/032764 A1 | 3/2010 |
| WO | WO 2011/070440 | 6/2011 |
| WO | WO-2012/103510 A2 | 8/2012 |
| WO | WO 2012/122649 | 9/2012 |

OTHER PUBLICATIONS

Galivo F et al. Single-cycle viral gene expression, rather than progressive replication and oncolysis, is required for VSV therapy of B16 melanoma. Gene Therapy 17:158-170, 2010.*
Morrison and Boyd. Organic Chemistry, 3rd Edition; Boston: Allyn and Bacon, Inc., pp. 412-413, (Year: 1974).*
Zhang J et al. Maraba MG1 virus enhances natural killer cell function via conventional dendritic cells to reduce postoperative metastatic disease. Molecular Therapy 22:1320-1332, (Year: 2014).*
Batenchuk et al., Non-replicating rhabdovirus-derived particles (NRRPs) eradicate acute leukemia by direct cytolysis and induction of antitumor immunity, Blood Cancer Journal, vol. 3:e123, Jul. 12, 2013.
Zajac P. et al., "Phase I/II clinical trial of a nonreplicative vaccinia virus expressing multiple HLA-A0201-restricted tumor-associated epitopes and costimulatory molecules in metastatic melanoma patients", Human Gene Therapy, vol. 14(16):1497-1510, Nov. 2003.
Kurooka et al., "Inactivated Sendai Virus Particles Eradicate Tumors by Inducing Immune Responses through Blocking Regulatory T Cells", Cancer Research, vol. 67(1):227-236, Jan. 2007.

(Continued)

*Primary Examiner* — Quang Nguyen
(74) *Attorney, Agent, or Firm* — Colleen M. Schaller; Howson & Howson LLP

(57) ABSTRACT

There is described herein a non-replicating Rhabdovirus-derived particle that lacks the ability to spread between cells while having tropism against immortalized cells. The non-replicating Rhabdovirus-derived particle may have cytolytic tropism against immortalized cells. There is also described a non-replicating Rhabdovirus-derived particle that lacks the ability to spread between cells but has innate and/or adaptive immune-stimulating properties.

7 Claims, 27 Drawing Sheets

Specification includes a Sequence Listing.

(56) References Cited

OTHER PUBLICATIONS

Bergman et al., "Preferential targeting of vesicular stomatitis virus to breast cancer cells", Virology, vol. 330(1):24-33, Dec. 2004.
Brun et al., "Identification of Genetically Modified Maraba Virus as an Oncolytic Rhabdovirus", Molecular Therapy, vol. 18(8):1440-1449, Aug. 2010.
Hastie et al., Vesicular stomatitis virus as a flexible platform for oncolytic virotherapy against cancer, Journal of General Virology, Dec. 2012;93(Pt 12):2529-45.
Delrue et al., Inactivated virus vaccines from chemistry to prophylaxis: merits, risks and challenges, Expert Review of Vaccines, Jun. 2012;11(6):695-719.
Anderson et al., Inactivated infectious haematopoietic necrosis virus (IHNV) vaccine, Journal of Fish Disease, Oct. 2008;31(10):729-45.
Kassis et al., Lyssavirus matrix protein induces apoptosis by a TRAIL-dependent mechanism involving caspase-8 activation, Journal of Virology, Jun. 2004;78(12):6543-55.
Wiktor et al., Immunogenicity of rabies virus inactivated by β-propiolactone, acetylethyleneimine, and ionizing irradiation, Applied Microbiology, May 1972;23(5):914-8.
Weck et al., Use of UV irradiation to identify the genetic information of vesicular stomatitis virus responsible for shu

DBT

PBS NRRPs

K1491

PBS NRRPs

GL261

PBS NRRPs

SEQUENCE LISTING

<160> NUMBER OF SEQ ID NOS: 5

<210> SEQ ID NO 1
<211> LENGTH: 495
<212> TYPE: PRT
<213> ORGANISM: Vesicular stomatitis virus
<300> PUBLICATION INFORMATION:
<308> DATABASE ACCESSION NUMBER: NCBI NP_955548
<309> DATABASE ENTRY DATE: 2000-12-05
<313> RELEVANT RESIDUES IN SEQ ID NO: (1)..(495)

<400> SEQUENCE: 1

```
Lys Phe Thr Ile Val Phe Pro His Asn Gln Lys Gly Asn Trp Lys Asn
1               5                   10                  15

Val Pro Ser Asn Tyr His Tyr Cys Pro Ser Ser Ser Asp Leu Asn Trp
            20                  25                  30

His Asn Asp Leu Ile Gly Thr Ala Ile Gln Val Lys Met Pro Lys Ser
        35                  40                  45

His Lys Ala Ile Gln Ala Asp Gly Trp Met Cys His Ala Ser Lys Trp
    50                  55                  60

Val Thr Thr Cys Asp Phe Arg Trp Tyr Gly Pro Lys Tyr Ile Thr Gln
65                  70                  75                  80

Ser Ile Arg Ser Phe Thr Pro Ser Val Glu Gln Cys Lys Glu Ser Ile
                85                  90                  95

Glu Gln Thr Lys Gln Gly Thr Trp Leu Asn Pro Gly Phe Pro Pro Gln
            100                 105                 110

Ser Cys Gly Tyr Ala Thr Val Thr Asp Ala Glu Ala Val Ile Val Gln
        115                 120                 125

Val Thr Pro His His Val Leu Val Asp Glu Tyr Thr Gly Glu Trp Val
130                 135                 140

Asp Ser Gln Phe Ile Asn Gly Lys Cys Ser Asn Tyr Ile Cys Pro Thr
145                 150                 155                 160

Val His Asn Ser Thr Thr Trp His Ser Asp Tyr Lys Val Lys Gly Leu
                165                 170                 175

Cys Asp Ser Asn Leu Ile Ser Met Asp Ile Thr Phe Phe Ser Glu Asp
            180                 185                 190

Gly Glu Leu Ser Ser Leu Gly Lys Glu Gly Thr Gly Phe Arg Ser Asn
        195                 200                 205

Tyr Phe Ala Tyr Glu Thr Gly Gly Lys Ala Cys Lys Met Gln Tyr Cys
    210                 215                 220

Lys His Trp Gly Val Arg Leu Pro Ser Gly Val Trp Phe Glu Met Ala
225                 230                 235                 240

Asp Lys Asp Leu Phe Ala Ala Ala Arg Phe Pro Glu Cys Pro Glu Gly
                245                 250                 255

Ser Ser Ile Ser Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala Gly Leu Pro Ile Ser Pro Val Asp Leu Ser Tyr
    290                 295                 300

Leu Ala Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Val Asp Ile Ala
                325                 330                 335

Ala Pro Ile Leu Ser Arg Met Val Gly Met Ile Ser Gly Thr Thr Thr
            340                 345                 350
```

```
Glu Arg Glu Leu Trp Asp Asp Trp Ala Pro Tyr Glu Asp Val Glu Ile
            355                 360                 365

Gly Pro Asn Gly Val Leu Arg Thr Ser Ser Gly Tyr Lys Phe Pro Leu
        370                 375                 380

Tyr Met Ile Gly His Gly Met Leu Asp Ser Asp Leu His Leu Ser Ser
385                 390                 395                 400

Lys Ala Gln Val Phe Glu His Pro His Ile Gln Asp Ala Ala Ser Gln
                405                 410                 415

Leu Pro Asp Asp Glu Ser Leu Phe Phe Gly Asp Thr Gly Leu Ser Lys
            420                 425                 430

Asn Pro Ile Glu Leu Val Glu Gly Trp Phe Ser Ser Trp Lys Ser Ser
        435                 440                 445

Ile Ala Ser Phe Phe Phe Ile Ile Gly Leu Ile Ile Gly Leu Phe Leu
    450                 455                 460

Val Leu Arg Val Gly Ile His Leu Cys Ile Lys Leu Lys His Thr Lys
465                 470                 475                 480

Lys Arg Gln Ile Tyr Thr Asp Ile Glu Met Asn Arg Leu Gly Lys
                485                 490                 495

<210> SEQ ID NO 2
<211> LENGTH: 422
<212> TYPE: PRT
<213> ORGANISM: Vesicular stomatitis virus
<300> PUBLICATION INFORMATION:
<308> DATABASE ACCESSION NUMBER: NCBI NP_041712
<309> DATABASE ENTRY DATE: 2000-12-05
<313> RELEVANT RESIDUES IN SEQ ID NO: (1)..(422)

<400> SEQUENCE: 2

Met Ser Val Thr Val Lys Arg Ile Ile Asp Asn Thr Val Ile Val Pro
1               5                   10                  15

Lys Leu Pro Ala Asn Glu Asp Pro Val Glu Tyr Pro Ala Asp Tyr Phe
            20                  25                  30

Arg Lys Ser Lys Glu Ile Pro Leu Tyr Ile Asn Thr Thr Lys Ser Leu
        35                  40                  45

Ser Asp Leu Arg Gly Tyr Val Tyr Gln Gly Leu Lys Ser Gly Asn Val
    50                  55                  60

Ser Ile Ile His Val Asn Ser Tyr Leu Tyr Gly Ala Leu Lys Asp Ile
65                  70                  75                  80

Arg Gly Lys Leu Asp Lys Asp Trp Ser Ser Phe Gly Ile Asn Ile Gly
                85                  90                  95

Lys Ala Gly Asp Thr Ile Gly Ile Phe Asp Leu Val Ser Leu Lys Ala
            100                 105                 110

Leu Asp Gly Val Leu Pro Asp Gly Val Ser Asp Ala Ser Arg Thr Ser
        115                 120                 125

Ala Asp Asp Lys Trp Leu Pro Leu Tyr Leu Leu Gly Leu Tyr Arg Val
    130                 135                 140

Gly Arg Thr Gln Met Pro Glu Tyr Arg Lys Lys Leu Met Asp Gly Leu
145                 150                 155                 160

Thr Asn Gln Cys Lys Met Ile Asn Glu Gln Phe Glu Pro Leu Val Pro
                165                 170                 175

Glu Gly Arg Asp Ile Phe Asp Val Trp Gly Asn Asp Ser Asn Tyr Thr
            180                 185                 190

Lys Ile Val Ala Ala Val Asp Met Phe Phe His Met Phe Lys Lys His
        195                 200                 205
```

```
Glu Cys Ala Ser Phe Arg Tyr Gly Thr Ile Val Ser Arg Phe Lys Asp
    210                 215                 220
Cys Ala Ala Leu Ala Thr Phe Gly His Leu Cys Lys Ile Thr Gly Met
225                 230                 235                 240
Ser Thr Glu Asp Val Thr Thr Trp Ile Leu Asn Arg Glu Val Ala Asp
                245                 250                 255
Glu Met Val Gln Met Met Leu Pro Gly Gln Glu Ile Asp Lys Ala Asp
                260                 265                 270
Ser Tyr Met Pro Tyr Leu Ile Asp Phe Gly Leu Ser Ser Lys Ser Pro
            275                 280                 285
Tyr Ser Ser Val Lys Asn Pro Ala Phe His Phe Trp Gly Gln Leu Thr
        290                 295                 300
Ala Leu Leu Leu Arg Ser Thr Arg Ala Arg Asn Ala Arg Gln Pro Asp
305                 310                 315                 320
Asp Ile Glu Tyr Thr Ser Leu Thr Thr Ala Gly Leu Leu Tyr Ala Tyr
                325                 330                 335
Ala Val Gly Ser Ser Ala Asp Leu Ala Gln Gln Phe Cys Val Gly Asp
                340                 345                 350
Asn Lys Tyr Thr Pro Asp Asp Ser Thr Gly Gly Leu Thr Thr Asn Ala
            355                 360                 365
Pro Pro Gln Gly Arg Asp Val Val Glu Trp Leu Gly Trp Phe Glu Asp
        370                 375                 380
Gln Asn Arg Lys Pro Thr Pro Asp Met Met Gln Tyr Ala Lys Arg Ala
385                 390                 395                 400
Val Met Ser Leu Gln Gly Leu Arg Glu Lys Thr Ile Gly Lys Tyr Ala
                405                 410                 415
Lys Ser Glu Phe Asp Lys
            420

<210> SEQ ID NO 3
<211> LENGTH: 265
<212> TYPE: PRT
<213> ORGANISM: Vesicular stomatitis virus
<300> PUBLICATION INFORMATION:
<308> DATABASE ACCESSION NUMBER: NCBI NP_041713
<309> DATABASE ENTRY DATE: 2000-12-05
<313> RELEVANT RESIDUES IN SEQ ID NO: (1)..(265)

<400> SEQUENCE: 3

Met Asp Asn Leu Thr Lys Val Arg Glu Tyr Leu Lys Ser Tyr Ser Arg
1               5                   10                  15
Leu Asp Gln Ala Val Gly Glu Ile Asp Glu Ile Glu Ala Gln Arg Ala
                20                  25                  30
Glu Lys Ser Asn Tyr Glu Leu Phe Gln Glu Asp Gly Val Glu Glu His
            35                  40                  45
Thr Lys Pro Ser Tyr Phe Gln Ala Ala Asp Asp Ser Asp Thr Glu Ser
        50                  55                  60
Glu Pro Glu Ile Glu Asp Asn Gln Gly Leu Tyr Ala Gln Asp Pro Glu
65                  70                  75                  80
Ala Glu Gln Val Glu Gly Phe Ile Gln Gly Pro Leu Asp Asp Tyr Ala
                85                  90                  95
Asp Glu Glu Val Asp Val Val Phe Thr Ser Asp Trp Lys Pro Pro Glu
                100                 105                 110
Leu Glu Ser Asp Glu His Gly Lys Thr Leu Arg Leu Thr Ser Pro Glu
            115                 120                 125
Gly Leu Ser Gly Glu Gln Lys Ser Gln Trp Leu Ser Thr Ile Lys Ala
```

```
            130                 135                 140
Val Val Gln Ser Ala Lys Tyr Trp Asn Leu Ala Glu Cys Thr Phe Glu
145                 150                 155                 160

Ala Ser Gly Glu Gly Val Ile Met Lys Glu Arg Gln Ile Thr Pro Asp
                165                 170                 175

Val Tyr Lys Val Thr Pro Val Met Asn Thr His Pro Ser Gln Ser Glu
                180                 185                 190

Ala Val Ser Asp Val Trp Ser Leu Ser Lys Thr Ser Met Thr Phe Gln
                195                 200                 205

Pro Lys Lys Ala Ser Leu Gln Pro Leu Thr Ile Ser Leu Asp Glu Leu
        210                 215                 220

Phe Ser Ser Arg Gly Glu Phe Ile Ser Val Gly Gly Asp Gly Arg Met
225                 230                 235                 240

Ser His Lys Glu Ala Ile Leu Leu Gly Leu Arg Tyr Lys Lys Leu Tyr
                245                 250                 255

Asn Gln Ala Arg Val Lys Tyr Ser Leu
                260                 265

<210> SEQ ID NO 4
<211> LENGTH: 229
<212> TYPE: PRT
<213> ORGANISM: Vesicular stomatitis virus
<300> PUBLICATION INFORMATION:
<308> DATABASE ACCESSION NUMBER: NCBI NP_041714.1
<309> DATABASE ENTRY DATE: 2000-12-05
<313> RELEVANT RESIDUES IN SEQ ID NO: (1)..(229)

<400> SEQUENCE: 4

Met Ser Ser Leu Lys Lys Ile Leu Gly Leu Lys Gly Lys Gly Lys Lys
1               5                   10                  15

Ser Lys Lys Leu Gly Ile Ala Pro Pro Tyr Glu Glu Asp Thr Ser
            20                  25                  30

Met Glu Tyr Ala Pro Ser Ala Pro Ile Asp Lys Ser Tyr Phe Gly Val
        35                  40                  45

Asp Glu Met Asp Thr Tyr Asp Pro Asn Gln Leu Arg Tyr Glu Lys Phe
    50                  55                  60

Phe Phe Thr Val Lys Met Thr Val Arg Ser Asn Arg Pro Phe Arg Thr
65                  70                  75                  80

Tyr Ser Asp Val Ala Ala Val Ser His Trp Asp His Met Tyr Ile
                85                  90                  95

Gly Met Ala Gly Lys Arg Pro Phe Tyr Lys Ile Leu Ala Phe Leu Gly
                100                 105                 110

Ser Ser Asn Leu Lys Ala Thr Pro Ala Val Leu Ala Asp Gln Gly Gln
        115                 120                 125

Pro Glu Tyr His Thr His Cys Glu Gly Arg Ala Tyr Leu Pro His Arg
    130                 135                 140

Met Gly Lys Thr Pro Pro Met Leu Asn Val Pro Glu His Phe Arg Arg
145                 150                 155                 160

Pro Phe Asn Ile Gly Leu Tyr Lys Gly Thr Ile Glu Leu Thr Met Thr
                165                 170                 175

Ile Tyr Asp Asp Glu Ser Leu Glu Ala Ala Pro Met Ile Trp Asp His
                180                 185                 190

Phe Asn Ser Ser Lys Phe Ser Asp Phe Arg Glu Lys Ala Leu Met Phe
        195                 200                 205

Gly Leu Ile Val Glu Lys Lys Ala Ser Gly Ala Trp Val Leu Asp Ser
    210                 215                 220
```

Ile Ser His Phe Lys
225

<210> SEQ ID NO 5
<211> LENGTH: 2109
<212> TYPE: PRT
<213> ORGANISM: Vesicular stomatitis virus
<300> PUBLICATION INFORMATION:
<308> DATABASE ACCESSION NUMBER: NCBI NC_041716.1
<309> DATABASE ENTRY DATE: 2000-12-05
<313> RELEVANT RESIDUES IN SEQ ID NO: (1)..(2109)

<400> SEQUENCE: 5

```
Met Glu Val His Asp Phe Glu Thr Asp Glu Phe Asn Asp Phe Asn Glu
1               5                   10                  15

Asp Asp Tyr Ala Thr Arg Glu Phe Leu Asn Pro Asp Glu Arg Met Thr
            20                  25                  30

Tyr Leu Asn His Ala Asp Tyr Asn Leu Asn Ser Pro Leu Ile Ser Asp
        35                  40                  45

Asp Ile Asp Asn Leu Ile Arg Lys Phe Asn Ser Leu Pro Ile Pro Ser
    50                  55                  60

Met Trp Asp Ser Lys Asn Trp Asp Gly Val Leu Glu Met Leu Thr Ser
65                  70                  75                  80

Cys Gln Ala Asn Pro Ile Ser Thr Ser Gln Met His Lys Trp Met Gly
                85                  90                  95

Ser Trp Leu Met Ser Asp Asn His Asp Ala Ser Gln Gly Tyr Ser Phe
            100                 105                 110

Leu His Glu Val Asp Lys Glu Ala Glu Ile Thr Phe Asp Val Val Glu
        115                 120                 125

Thr Phe Ile Arg Gly Trp Gly Asn Lys Pro Ile Glu Tyr Ile Lys Lys
    130                 135                 140

Glu Arg Trp Thr Asp Ser Phe Lys Ile Leu Ala Tyr Leu Cys Gln Lys
145                 150                 155                 160

Phe Leu Asp Leu His Lys Leu Thr Leu Ile Leu Asn Ala Val Ser Glu
                165                 170                 175

Val Glu Leu Leu Asn Leu Ala Arg Thr Phe Lys Gly Lys Val Arg Arg
            180                 185                 190

Ser Ser His Gly Thr Asn Ile Cys Arg Ile Arg Val Pro Ser Leu Gly
        195                 200                 205

Pro Thr Phe Ile Ser Glu Gly Trp Ala Tyr Phe Lys Lys Leu Asp Ile
    210                 215                 220

Leu Met Asp Arg Asn Phe Leu Leu Met Val Lys Asp Val Ile Ile Gly
225                 230                 235                 240

Arg Met Gln Thr Val Leu Ser Met Val Cys Arg Ile Asp Asn Leu Phe
                245                 250                 255

Ser Glu Gln Asp Ile Phe Ser Leu Leu Asn Ile Tyr Arg Ile Gly Asp
            260                 265                 270

Lys Ile Val Glu Arg Gln Gly Asn Phe Ser Tyr Asp Leu Ile Lys Met
        275                 280                 285

Val Glu Pro Ile Cys Asn Leu Lys Leu Met Lys Leu Ala Arg Glu Ser
    290                 295                 300

Arg Pro Leu Val Pro Gln Phe Pro His Phe Glu Asn His Ile Lys Thr
305                 310                 315                 320

Ser Val Asp Glu Gly Ala Lys Ile Asp Arg Gly Ile Arg Phe Leu His
                325                 330                 335
```

```
Asp Gln Ile Met Ser Val Lys Thr Val Asp Leu Thr Leu Val Ile Tyr
            340                 345                 350
Gly Ser Phe Arg His Trp Gly His Pro Phe Ile Asp Tyr Tyr Thr Gly
        355                 360                 365
Leu Glu Lys Leu His Ser Gln Val Thr Met Lys Lys Asp Ile Asp Val
    370                 375                 380
Ser Tyr Ala Lys Ala Leu Ala Ser Asp Leu Ala Arg Ile Val Leu Phe
385                 390                 395                 400
Gln Gln Phe Asn Asp His Lys Lys Trp Phe Val Asn Gly Asp Leu Leu
                405                 410                 415
Pro His Asp His Pro Phe Lys Ser His Val Lys Glu Asn Thr Trp Pro
            420                 425                 430
Thr Ala Ala Gln Val Gln Asp Phe Gly Asp Lys Trp His Glu Leu Pro
        435                 440                 445
Leu Ile Lys Cys Phe Glu Ile Pro Asp Leu Leu Asp Pro Ser Ile Ile
    450                 455                 460
Tyr Ser Asp Lys Ser His Ser Met Asn Arg Ser Glu Val Leu Lys His
465                 470                 475                 480
Val Arg Met Asn Pro Asn Thr Pro Ile Pro Ser Lys Lys Val Leu Gln
                485                 490                 495
Thr Met Leu Asp Thr Lys Ala Thr Asn Trp Lys Glu Phe Leu Lys Glu
            500                 505                 510
Ile Asp Glu Lys Gly Leu Asp Asp Asp Leu Ile Ile Gly Leu Lys
        515                 520                 525
Gly Lys Glu Arg Glu Leu Lys Leu Ala Gly Arg Phe Phe Ser Leu Met
    530                 535                 540
Ser Trp Lys Leu Arg Glu Tyr Phe Val Ile Thr Glu Tyr Leu Ile Lys
545                 550                 555                 560
Thr His Phe Val Pro Met Phe Lys Gly Leu Thr Met Ala Asp Asp Leu
                565                 570                 575
Thr Ala Val Ile Lys Lys Met Leu Asp Ser Ser Gly Gln Gly Leu
            580                 585                 590
Lys Ser Tyr Glu Ala Ile Cys Ile Ala Asn His Ile Asp Tyr Glu Lys
    595                 600                 605
Trp Asn Asn His Gln Arg Lys Leu Ser Asn Gly Pro Val Phe Arg Val
610                 615                 620
Met Gly Gln Phe Leu Gly Tyr Pro Ser Leu Ile Glu Arg Thr His Glu
625                 630                 635                 640
Phe Phe Glu Lys Ser Leu Ile Tyr Tyr Asn Gly Arg Pro Asp Leu Met
                645                 650                 655
Arg Val His Asn Asn Thr Leu Ile Asn Ser Thr Ser Gln Arg Val Cys
            660                 665                 670
Trp Gln Gly Gln Glu Gly Gly Leu Glu Gly Leu Arg Gln Lys Gly Trp
        675                 680                 685
Thr Ile Leu Asn Leu Leu Val Ile Gln Arg Glu Ala Lys Ile Arg Asn
    690                 695                 700
Thr Ala Val Lys Val Leu Ala Gln Gly Asp Asn Gln Val Ile Cys Thr
705                 710                 715                 720
Gln Tyr Lys Thr Lys Lys Ser Arg Asn Val Val Glu Leu Gln Gly Ala
                725                 730                 735
Leu Asn Gln Met Val Ser Asn Asn Glu Lys Ile Met Thr Ala Ile Lys
            740                 745                 750
Ile Gly Thr Gly Lys Leu Gly Leu Leu Ile Asn Asp Asp Glu Thr Met
```

-continued

```
            755                 760                 765
Gln Ser Ala Asp Tyr Leu Asn Tyr Gly Lys Ile Pro Ile Phe Arg Gly
770                 775                 780

Val Ile Arg Gly Leu Glu Thr Lys Arg Trp Ser Arg Val Thr Cys Val
785                 790                 795                 800

Thr Asn Asp Gln Ile Pro Thr Cys Ala Asn Ile Met Ser Ser Val Ser
                    805                 810                 815

Thr Asn Ala Leu Thr Val Ala His Phe Ala Glu Asn Pro Ile Asn Ala
                820                 825                 830

Met Ile Gln Tyr Asn Tyr Phe Gly Thr Phe Ala Arg Leu Leu Leu Met
            835                 840                 845

Met His Asp Pro Ala Leu Arg Gln Ser Leu Tyr Glu Val Gln Asp Lys
850                 855                 860

Ile Pro Gly Leu His Ser Ser Thr Phe Lys Tyr Ala Met Leu Tyr Leu
865                 870                 875                 880

Asp Pro Ser Ile Gly Gly Val Ser Gly Met Ser Leu Ser Arg Phe Leu
                    885                 890                 895

Ile Arg Ala Phe Pro Asp Pro Val Thr Glu Ser Leu Ser Phe Trp Arg
                900                 905                 910

Phe Ile His Val His Ala Arg Ser Glu His Leu Lys Glu Met Ser Ala
            915                 920                 925

Val Phe Gly Asn Pro Glu Ile Ala Lys Phe Arg Ile Thr His Ile Asp
930                 935                 940

Lys Leu Val Glu Asp Pro Thr Ser Leu Asn Ile Ala Met Gly Met Ser
945                 950                 955                 960

Pro Ala Asn Leu Leu Lys Thr Glu Val Lys Lys Cys Leu Ile Glu Ser
                    965                 970                 975

Arg Gln Thr Ile Arg Asn Gln Val Ile Lys Asp Ala Thr Ile Tyr Leu
                980                 985                 990

Tyr His Glu Glu Asp Arg Leu Arg  Ser Phe Leu Trp Ser  Ile Asn Pro
            995                  1000                1005

Leu Phe  Pro Arg Phe Leu Ser  Glu Phe Lys Ser Gly  Thr Phe Leu
1010                1015                1020

Gly Val  Ala Asp Gly Leu Ile  Ser Leu Phe Gln Asn  Ser Arg Thr
1025                1030                1035

Ile Arg  Asn Ser Phe Lys Lys  Lys Tyr His Arg Glu  Leu Asp Asp
1040                1045                1050

Leu Ile  Val Arg Ser Glu Val  Ser Ser Leu Thr His  Leu Gly Lys
1055                1060                1065

Leu His  Leu Arg Arg Gly Ser  Cys Lys Met Trp Thr  Cys Ser Ala
1070                1075                1080

Thr His  Ala Asp Thr Leu Arg  Tyr Lys Ser Trp Gly  Arg Thr Val
1085                1090                1095

Ile Gly  Thr Thr Val Pro His  Pro Leu Glu Met Leu  Gly Pro Gln
1100                1105                1110

His Arg  Lys Glu Thr Pro Cys  Ala Pro Cys Asn Thr  Ser Gly Phe
1115                1120                1125

Asn Tyr  Val Ser Val His Cys  Pro Asp Gly Ile His  Asp Val Phe
1130                1135                1140

Ser Ser  Arg Gly Pro Leu Pro  Ala Tyr Leu Gly Ser  Lys Thr Ser
1145                1150                1155

Glu Ser  Thr Ser Ile Leu Gln  Pro Trp Glu Arg Glu  Ser Lys Val
1160                1165                1170
```

```
Pro Leu Ile Lys Arg Ala Thr Arg Leu Arg Asp Ala Ile Ser Trp
    1175            1180                1185

Phe Val Glu Pro Asp Ser Lys Leu Ala Met Thr Ile Leu Ser Asn
    1190            1195                1200

Ile His Ser Leu Thr Gly Glu Glu Trp Thr Lys Arg Gln His Gly
    1205            1210                1215

Phe Lys Arg Thr Gly Ser Ala Leu His Arg Phe Ser Thr Ser Arg
    1220            1225                1230

Met Ser His Gly Gly Phe Ala Ser Gln Ser Thr Ala Ala Leu Thr
    1235            1240                1245

Arg Leu Met Ala Thr Thr Asp Thr Met Arg Asp Leu Gly Asp Gln
    1250            1255                1260

Asn Phe Asp Phe Leu Phe Gln Ala Thr Leu Leu Tyr Ala Gln Ile
    1265            1270                1275

Thr Thr Thr Val Ala Arg Asp Gly Trp Ile Thr Ser Cys Thr Asp
    1280            1285                1290

His Tyr His Ile Ala Cys Lys Ser Cys Leu Arg Pro Ile Glu Glu
    1295            1300                1305

Ile Thr Leu Asp Ser Ser Met Asp Tyr Thr Pro Pro Asp Val Ser
    1310            1315                1320

His Val Leu Lys Thr Trp Arg Asn Gly Glu Gly Ser Trp Gly Gln
    1325            1330                1335

Glu Ile Lys Gln Ile Tyr Pro Leu Glu Gly Asn Trp Lys Asn Leu
    1340            1345                1350

Ala Pro Ala Glu Gln Ser Tyr Gln Val Gly Arg Cys Ile Gly Phe
    1355            1360                1365

Leu Tyr Gly Asp Leu Ala Tyr Arg Lys Ser Thr His Ala Glu Asp
    1370            1375                1380

Ser Ser Leu Phe Pro Leu Ser Ile Gln Gly Arg Ile Arg Gly Arg
    1385            1390                1395

Gly Phe Leu Lys Gly Leu Leu Asp Gly Leu Met Arg Ala Ser Cys
    1400            1405                1410

Cys Gln Val Ile His Arg Arg Ser Leu Ala His Leu Lys Arg Pro
    1415            1420                1425

Ala Asn Ala Val Tyr Gly Gly Leu Ile Tyr Leu Ile Asp Lys Leu
    1430            1435                1440

Ser Val Ser Pro Pro Phe Leu Ser Leu Thr Arg Ser Gly Pro Ile
    1445            1450                1455

Arg Asp Glu Leu Glu Thr Ile Pro His Lys Ile Pro Thr Ser Tyr
    1460            1465                1470

Pro Thr Ser Asn Arg Asp Met Gly Val Ile Val Arg Asn Tyr Phe
    1475            1480                1485

Lys Tyr Gln Cys Arg Leu Ile Glu Lys Gly Lys Tyr Arg Ser His
    1490            1495                1500

Tyr Ser Gln Leu Trp Leu Phe Ser Asp Val Leu Ser Ile Asp Phe
    1505            1510                1515

Ile Gly Pro Phe Ser Ile Ser Thr Thr Leu Leu Gln Ile Leu Tyr
    1520            1525                1530

Lys Pro Phe Leu Ser Gly Lys Asp Lys Asn Glu Leu Arg Glu Leu
    1535            1540                1545

Ala Asn Leu Ser Ser Leu Leu Arg Ser Gly Glu Gly Trp Glu Asp
    1550            1555                1560
```

```
Ile His Val Lys Phe Phe Thr Lys Asp Ile Leu Leu Cys Pro Glu
1565                1570                1575

Glu Ile Arg His Ala Cys Lys Phe Gly Ile Ala Lys Asp Asn Asn
    1580                1585                1590

Lys Asp Met Ser Tyr Pro Pro Trp Gly Arg Glu Ser Arg Gly Thr
1595                1600                1605

Ile Thr Thr Ile Pro Val Tyr Tyr Thr Thr Pro Tyr Pro Lys
    1610                1615                1620

Met Leu Glu Met Pro Pro Arg Ile Gln Asn Pro Leu Leu Ser Gly
    1625                1630                1635

Ile Arg Leu Gly Gln Leu Pro Thr Gly Ala His Tyr Lys Ile Arg
    1640                1645                1650

Ser Ile Leu His Gly Met Gly Ile His Tyr Arg Asp Phe Leu Ser
    1655                1660                1665

Cys Gly Asp Gly Ser Gly Gly Met Thr Ala Ala Leu Leu Arg Glu
    1670                1675                1680

Asn Val His Ser Arg Gly Ile Phe Asn Ser Leu Leu Glu Leu Ser
    1685                1690                1695

Gly Ser Val Met Arg Gly Ala Ser Pro Glu Pro Ser Ala Leu
    1700                1705                1710

Glu Thr Leu Gly Gly Asp Lys Ser Arg Cys Val Asn Gly Glu Thr
    1715                1720                1725

Cys Trp Glu Tyr Pro Ser Asp Leu Cys Asp Pro Arg Thr Trp Asp
    1730                1735                1740

Tyr Phe Leu Arg Leu Lys Ala Gly Leu Gly Leu Gln Ile Asp Leu
    1745                1750                1755

Ile Val Met Asp Met Glu Val Arg Asp Ser Ser Thr Ser Leu Lys
    1760                1765                1770

Ile Glu Thr Asn Val Arg Asn Tyr Val His Arg Ile Leu Asp Glu
    1775                1780                1785

Gln Gly Val Leu Ile Tyr Lys Thr Tyr Gly Thr Tyr Ile Cys Glu
    1790                1795                1800

Ser Glu Lys Asn Ala Val Thr Ile Leu Gly Pro Met Phe Lys Thr
    1805                1810                1815

Val Asp Leu Val Gln Thr Glu Phe Ser Ser Ser Gln Thr Ser Glu
    1820                1825                1830

Val Tyr Met Val Cys Lys Gly Leu Lys Lys Leu Ile Asp Glu Pro
    1835                1840                1845

Asn Pro Asp Trp Ser Ser Ile Asn Glu Ser Trp Lys Asn Leu Tyr
    1850                1855                1860

Ala Phe Gln Ser Ser Glu Gln Glu Phe Ala Arg Ala Lys Lys Val
    1865                1870                1875

Ser Thr Tyr Phe Thr Leu Thr Gly Ile Pro Ser Gln Phe Ile Pro
    1880                1885                1890

Asp Pro Phe Val Asn Ile Glu Thr Met Leu Gln Ile Phe Gly Val
    1895                1900                1905

Pro Thr Gly Val Ser His Ala Ala Leu Lys Ser Ser Asp Arg
    1910                1915                1920

Pro Ala Asp Leu Leu Thr Ile Ser Leu Phe Tyr Met Ala Ile Ile
    1925                1930                1935

Ser Tyr Tyr Asn Ile Asn His Ile Arg Val Gly Pro Ile Pro Pro
    1940                1945                1950

Asn Pro Pro Ser Asp Gly Ile Ala Gln Asn Val Gly Ile Ala Ile
```

-continued

```
      1955               1960              1965
Thr Gly Ile Ser Phe Trp Leu Ser Leu Met Glu Lys Asp Ile Pro
    1970              1975              1980
Leu Tyr Gln Gln Cys Leu Ala Val Ile Gln Gln Ser Phe Pro Ile
    1985              1990              1995
Arg Trp Glu Ala Val Ser Val Lys Gly Gly Tyr Lys Gln Lys Trp
    2000              2005              2010
Ser Thr Arg Gly Asp Gly Leu Pro Lys Asp Thr Arg Thr Ser Asp
    2015              2020              2025
Ser Leu Ala Pro Ile Gly Asn Trp Ile Arg Ser Leu Glu Leu Val
    2030              2035              2040
Arg Asn Gln Val Arg Leu Asn Pro Phe Asn Glu Ile Leu Phe Asn
    2045              2050              2055
Gln Leu Cys Arg Thr Val Asp Asn His Leu Lys Trp Ser Asn Leu
    2060              2065              2070
Arg Arg Asn Thr Gly Met Ile Glu Trp Ile Asn Arg Arg Ile Ser
    2075              2080              2085
Lys Glu Asp Arg Ser Ile Leu Met Leu Lys Ser Asp Leu His Glu
    2090              2095              2100
Glu Asn Ser Trp Arg Asp
    2105
```

NON-REPLICATING VIRUS-DERIVED PARTICLES AND USES THEREOF

CROSS-REFERENCE TO RELATED APPLICATIONS

This application is a US national phase of International Patent Application No. PCT/CA2013/051009, filed Dec. 20, 2013, which claims the benefit of priority of U.S. Provisional Patent Application No. 61/740,856 filed Dec. 21, 2012 and of U.S. Provisional Patent Application No. 61/835,310 filed Jun. 14, 2013, which are incorporated herein by reference in their entirety.

FIELD

The present disclosure relates generally to a non-replicating virus-derived particle and its use as an anti-cancer agent.

BACKGROUND

The following background discussion does not imply or admit that anything described below is prior art or part of the knowledge of people skilled in the art in any country.

Oncolytic viruses (OVs) have been engineered through attenuating mutations or deletions which allow the virus to replicate exclusively in cells associated with an impaired immune response or enhanced metabolic activity, two key characteristics of tumorigenesis. Examples of current advanced oncolytic therapeutics include the Herpes Simplex Virus OncoVEXGM-CSF and the vaccinia virus (JX594). To date, the main focus of the OV field has been the development of platforms where the live virus has preferential replication/spreading capacity within the local tumor environment.

Rhabdoviruses viruses (RVs), such as vesicular stomatitis virus (VSV) and Maraba, are currently being explored as anti-cancer therapeutics. In tumors, viral propagation is enabled by unrestrained metabolic activities and impaired anti-viral programs. Tumor susceptibility to RV treatment is further enhanced due to pre-disposition towards virus-mediated apoptosis.

In the Rhabdovirus field, oncolytic platforms developed to date utilize a replication competent virus where the virus spreads between tumor cells. In fact, reports describing the use of live replication/expression competent rhabdovirus as a direct virotherapy for cancer typically compare efficacy to non-replicating/non-expressing virus controls where no measurable efficacy is observed. In these reports, it is concluded that Rhabdovirus genome replication and/or expression is a critical and essential component of tumor cytotoxicity and therapeutic efficacy.

The lack of oncolytic effects in these previous studies is reflected in the methods used to disrupt virus genome replication and/or expression as well as in the number of virus particles used. Indeed, when these previous methods are used to disrupt virus genome replication and/or expression, no bioactivity of the virus is observed. Furthermore, in these studies, non-replicating virus controls are applied at the same dose as their live virus counterparts, and not at higher doses to ensure that each cell encounters a non-replicating particle.

Alternative, and preferably more effective, approaches are desired to treat and cure most forms of cancers. For example, the outcome for the majority of adult patients suffering from acute lymphoblastic or acute myeloid leukemia remains dismal. This is in part due to the significant immunocompromised nature of the disease. For a minority of patients, anti-tumor immune responses are partially restored through allogeneic stem cell transplantation after myeloablative conditioning. This therapy is potentially curative, however is associated with frequent adverse events and significant treatment-related mortality. For many patients with chronic-phase chronic myeloid leukemia (CML), targeted tyrosine kinase inhibitor (TKI) therapy offers excellent disease control. However when progression into acute leukemic blast crisis occurs, very limited therapeutic options exist due to development of multi-drug resistance and the rapid kinetics of this form of recalcitrant leukemia.

Hence there is need for alternative anti-cancer agents, particularly for immunocompromised patients. The anti-cancer agent, by virtue of its design and components, would preferably be able to address current unmet clinical needs and/or overcome at least some of the above-discussed problems.

SUMMARY

The following summary is intended to introduce the reader to one or more inventions described herein, but not to define any of them. Inventions may reside in any combination of features described anywhere in this document.

While live OV strategies are being pursued to treat a variety of tumor types, their application in hematopoietic malignancies in particular is complicated by several factors. Limited virion production and reduced spread between leukemia cells requires high-dose viral therapy to overcome these inefficiencies. However, uncontrolled live virus spread and off-target effects in normal tissue compromise the safety of this approach, particularly in immunosuppressed patients.

Issues associated with using live virus include: 1) safety, which relies on the ability of the live Rhabdovirus to spread only in diseased tumor tissue, leaving healthy tissue alone; 2) low doses for administration, since the introduction of live spreadable virus to a patient requires the administration of relatively low doses of these live viral agents to ensure safety; 3) immune diversion from the tumor towards the live virus which effectively decreases the efficiency of anti-tumor immune responses; and 4) engineered live viruses designed with proclivity for tumor often have impaired production capacity compared to wild type virus, and consequently, formulation efficiencies and production costs are sub-optimal from a manufacturing perspective.

It has been previously shown that intra-tumoral injection with VSV engineered to have a deletion of the glycoprotein gene (VSVΔG), which prevents final virion assembly and spread, elicits anti-tumor immune responses. However, treatment with VSVΔG cannot provide a significant reduction of disseminated tumor bulk, partly due to the inability to manufacture and deliver therapeutically effective doses.

The authors are aware of no reports that detail the use of a non-replicating and non-expressing Rhabdovirus-derived platform as an anti-cancer therapeutic. Non-replicating virus-derived particles (NVRP) of the present disclosure, and non-replicating rhabdovirus-derived particles (NRRP) in particular, are wild type virus particles modified so as to lack the ability to spread between cells. Once modified, the non-replicating virus-derived particle (NVRP) cannot sustain virion replication.

NVRPs are unique in that they retain tropism, such as cytolytic tropism, against immortalized cells. This means that NVRPs will induce cell death preferentially in immortalized cells such as tumor or cancer cells and transformed immortalized cells. Specific examples of NVRPs have innate and/or adaptive immune-stimulating properties against immortalized cells.

In one aspect, the present disclosure describes a non-replicating rhabdovirus-derived particle that lacks the ability to spread between cells while having tropism against immortalized cells. The tropism may be a cytolytic tropism. The non-replicating rhabdovirus-derived particle may have innate or adaptive immune-stimulating properties against immortalized cells.

In yet another aspect, the present disclosure provides a use of a non-replicating rhabdovirus-derived particle to treat a population of hyperproliferative cells or cancer cells. The population of hyperproliferative cells is preferably of hematopoietic nature, and preferably leukemic cells. The population of hyperproliferative cells may be solid tumor cells.

In still another aspect, the present disclosure describes a method of treating a patient having a population of hyperproliferative cells or cancer cells. The method includes administering to the patient non-replicating rhabdovirus-derived particles. The population of hyperproliferative cells may preferably be of hematopoietic nature, preferably leukemic cells. The population of hyperproliferative cells may be solid tumor cells.

Other aspects and features of the present disclosure will become apparent to those ordinarily skilled in the art upon review of the following description of specific embodiments in conjunction with the accompanying figures.

BRIEF DESCRIPTION OF DRAWINGS

Embodiments of the present disclosure will now be described, by way of example only, with reference to the attached Figures.

DETAILED DESCRIPTION

Figure 1A:
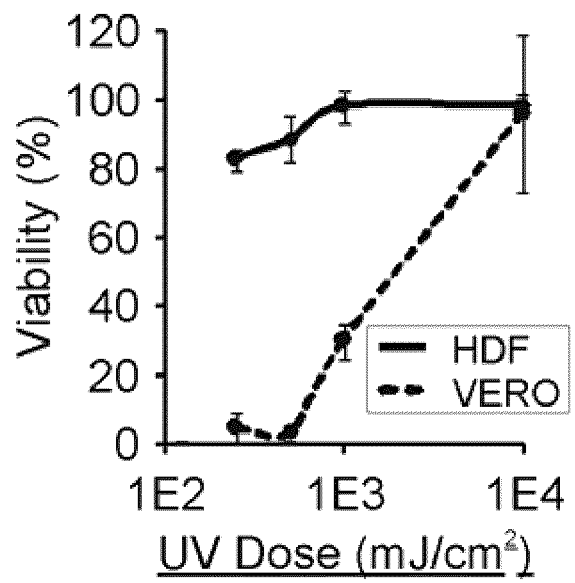
FIG. 1A is a graph showing the impact of UV dosage on NRRP-mediated cytotoxicity on Vero and HDFN cells. No GFP signal was detected following UV-induced NRRP generation. Viability was quantified using the resazurin assay 72 h post infection. The MOI of this experiment was set at 100 particles per cell. Error bars represent the standard deviation between triplicate experiments.

Generally, the present disclosure provides a non-replicating virus-derived particle and its use as an anti-cancer agent. A non-replicating virus-derived particle (NRVP) is a virus-derived particle that is able to bind and be internalized by a cell, but has been modified to prevent formation, or substantially reduce formation, of new virus particles when the NRVP is in the cell. One example of a NRVP is a non-replicating rhabdovirus-derived particle (NRRP).

The NRVP includes: an envelope having a sufficient number of functional G proteins on the surface of the envelope to allow the virus-derived particle to bind a surface of a cell and be internalized. It also includes an RNA polynucleotide with a sequence that encodes all the proteins required for new virus particle assembly, and a mixture of proteins that form a structure around the RNA polynucleotide. However, the RNA structure of the NRVP is sufficiently cross-linked, or has been cleaved to form discontinuous segments of RNA, such that the NRVP genome is unable be used to produce the proteins required for new virus formation. For example, the RNA sequence may not be transcribed into mRNA, translated into protein, or both when the particle is in a cell. The impairment or lack of transcription and/or translation means that insufficient proteins are produced in the cell and new virus particles cannot be assembled.

The functional G protein may have a sequence that includes SEQ ID NO: 1, shown below, which is the sequence of the glycoprotein mature peptide of vesicular stomatitis Indiana virus. This functional G protein has NCBI accession number NP 955548.1.

```
                                               (SEQ ID NO: 1)
kftivfphnq kgnwknvpsn yhycpsssdl nwhndligta iqvkmpkshk aiqadgwmch askwvttcdf rwygpkyitq sirsftpsve qckesieqtk qgtwlnpgfp pqscgyatvt daeavivqvt phhvlvdeyt gewvdsgfin gkcsnyicpt vhnsttwhsd ykvkglcdsn lismditffs edgelsslgk egtgfrsnyf ayetggkack mqyckhwgvr lpsgvwfema dkdlfaaarf pecpegssis apsqtsvdvs liqdverild yslcqetwsk iraglpispv dlsylapknp gtgpaftiin gtlkyfetry irvdiaapil srmvgmisgt tterelwddw apyedveigp ngvlrtssgy kfplymighg mldsdlhlss kaqvfehphi qdaasqlpdd eslffgdtgl sknpielveg wfsswkssia sfffiiglii glflvlrvgi hlciklkhtk krqiytdiem nrlgk
```

Alternatively, the functional G protein may have a sequence that is at least 75% identical to SEQ ID NO: 1 so long as it is capable of binding to a surface of a cell and effecting internalization of the particle. For example, conservative substitutions of amino acids may be made without abrogating the ability of the protein to bind to the surface of a cell and effect internalization of the particle. Examples of conservative substitutions are shown below in Table 1.

TABLE 1

Conservative Amino Acid Substitutions

| Original Residues | Exemplary Substitutions | Preferred Substitutions |
| --- | --- | --- |
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

Less conservative substitutions may be made in portions of the G protein that do not take part in the cell surface binding (such as in a trans-membrane domain), while more conservative substitutions might be required in portions of the protein that interact with a G protein receptor. G proteins are known in the art and a skilled person would be able to determine what amino acid substitutions would be possible without abrogating the ability of the protein to bind to the surface of a cell and effect internalization of the particle.

The mixture of proteins that form a structure around the RNA may include at least N, P, M, and L proteins. A NRVP having N, P, M, G and L proteins may include rhabdovirus-derived NRVP. Rhadbovirus-derived NRVPs may be referred to as non-replicating rhabdovirus-derived particles (NRRPs). For the purposes of the present disclosure, the term "Rhabdovirus" (NCBI Taxonomy ID: 11270) may include any one of the following genus of viruses and variants thereof: Cytorhabdovirus (NCBI Taxonomy ID: 11305), Ephemerovirus (NCBI Taxonomy ID: 32613), Vesiculovirus (NCBI Taxonomy ID: 11271), unclassified Dimarhabdovirussupergroup (NCBI Taxonomy ID: 349166), Lyssavirus (NCBI Taxonomy ID: 11286), Novirhabdovirus (NCBI Taxonomy ID: 186778), Nucleorhabdovirus (NCBI Taxonomy ID: 11306), unassigned rhabdovirus (NCBI Taxonomy ID: 686606) and unclassified rhabdovirus (NCBI Taxonomy ID: 35303). Species within the Rhabdovirus family include, but are not limited to, Maraba virus, Vesicular stomatitis virus (VSV) and Farmington virus.

The N protein may have a sequence that includes SEQ ID NO: 2, shown below, which is the sequence of the nucleocapsid protein of vesicular stomatitis Indiana virus. This N protein has NCBI accession number NC 041712.1.

```
                                               (SEQ ID NO: 2)
msvtvkriid ntvivpklpa nedpveypad yfrkskeipl yinttkslsd lrgyvyqglk sgnvsiihvn sylygalkdi rgkldkdwss fginigkagd tigifdlvsl kaldgvlpdg vsdasrtsad dkwlplyllg lyrvgrtqmp eyrkklmdgl tnqckmineq feplvpegrd ifdvwgndsn ytkivaavdm ffhmfkkhec asfrygtivs rfkdcaalat fghlckitgm stedvttwil nrevademvq mmlpgqeidk adsympylid fglsskspys svknpafhfw gqltalllrs trarnarqpd
```

```
dieytsltta gllyayavgs sadlaqqfcv gdnkytpdds tgglttnapp qgrdvvewlg wfedqnrkpt pdmmqyakra vmslqglrek tigkyaksef dk
```

Alternatively, the N protein may have a sequence that is at least 80% identical to SEQ ID NO: 2 so long as it is capable of participating in the formation of the protein structure. For example, conservative substitutions of amino acids may be made without abrogating the ability of the protein to participate in the formation of the protein structure. Examples of conservative substitutions are shown in Table 1.

The P protein may have a sequence that includes SEQ ID NO: 3, shown below, which is the sequence of the NS protein of vesicular stomatitis Indiana virus. This P protein has NCBI accession number NC 041713.1.

```
                                              (SEQ ID NO: 3)
mdnitkvrey lksysrldqa vgeideieaq raeksnyelf qedgveehtk psyfqaadds dtesepeied ngglyaqdpe aeqvegfiqg plddyadeev dvvftsdwkp pelesdehgk tlrltspegl sgeqksqwls tikavvqsak ywnlaectfe asgegvimke rqitpdvykv tpvmnthpsq seavsdvwsl sktsmtfqpk kaslqpltis ldelfssrge fisvggdgrm shkeaillgl rykklynqar vkysl
```

Alternatively, the P protein may have a sequence that is at least 80% identical to SEQ ID NO: 3 so long as it is capable of participating in the formation of the protein structure. For example, conservative substitutions of amino acids may be made without abrogating the ability of the protein to participate in the formation of the protein structure. Examples of conservative substitutions are shown in Table 1.

The M protein may have a sequence that includes SEQ ID NO: 4, shown below, which is the sequence of the matrix protein of vesicular stomatitis Indiana virus. This M protein has NCBI accession number NC 041714.1.

```
                                              (SEQ ID NO: 4)
msslkkilgl kgkgkkskkl giapppyeed tsmeyapsap idksyfgvde mdtydpnqlr yekffftvkm tvrsnrpfrt ysdvaaavsh wdhmyigmag krpfykilaf lgssnlkatp avladqgqpe yhthcegray lphrmgktpp mlnvpehfrr pfniglykgt ieltmtiydd esleaapmiw dhfnsskfsd frekalmfgl ivekkasgaw vldsishfk
```

Alternatively, the M protein may have a sequence that is at least 80% identical to SEQ ID NO: 4 so long as it is capable of participating in the formation of the protein structure. For example, conservative substitutions of amino acids may be made without abrogating the ability of the protein to participate in the formation of the protein structure. Examples of conservative substitutions are shown in Table 1.

The L protein may have a sequence that includes SEQ ID NO: 5, shown below, which is the sequence of the polymerase protein of vesicular stomatitis Indiana virus. This L protein has NCBI accession number NC 041716.1.

```
                                              (SEQ ID NO: 5)
mevhdfetde fndfneddya treflnpder mtylnhadyn lnsplisddi dnlirkfnsl pipsmwdskn wdgvlemlts cqanpistsq mhkwmgswlm sdnhdasqgy sflhevdkea eitfdvvetf irgwgnkpie yikkerwtds fkilaylcqk fldlhkltli lnavsevell nlartfkgkv rrsshgtnic rirvpslgpt fisegwayfk kldilmdrnf llmvkdviig rmqtvlsmvc ridnlfseqd ifsllniyri gdkiverqgn fsydlikmve picnlklmkl aresrplvpq fphfenhikt svdegakidr girflhdqim svktvdltlv iygsfrhwgh pfidyytgle klhsqvtmkk didvsyakal asdlarivlf qqfndhkkwf vngdllphdh pfkshvkent wptaaqvqdf gdkwhelpli kcfeipdlld psiiysdksh smnrsevlkh vrmnpntpip skkvlqtmld tkatnwkefl keidekgldd ddliiglkgk erelklagrf fslmswklre yfviteylik thfvpmfkgl tmaddltavi kkmldsssgq glksyeaici anhidyekwn nhqrklsngp vfrvmgqflg ypslierthe ffeksliyyn grpdlmrvhn ntlinstsqr vcwqgqeggl eglrqkgwti lnllviqrea kirntavkvl aqgdnqvict qyktkksrnv velqgalnqm vsnnekimta ikigtgklgl linddetmqs adylnygkip ifrgvirgle tkrwsrvtcv tndqiptcan imssvstnal tvahfaenpi namiqynyfg tfarlllmmh dpalrqslye vqdkipglhs stfkyamlyl dpsiggvsgm slsrfliraf pdpvteslsf wrfihvhars ehlkemsavf gnpeiakfri thidklvedp tslniamgms panllktevk kcliesrqti rnqvikdati ylyheedrlr sflwsinplf prflsefksg tflgvadgli slfqnsrtir nsfkkkyhre ldddlivrsev sslthlgklh lrrgsckmwt csathadtlr ykswgrtvig ttvphpleml gpqhrketpc apcntsgfny vsvhcpdgih dvfssrgplp aylgsktses tsilqpwere skvplikrat rlrdaiswfv epdsklamti lsnihsltge ewtkrqhgfk rtgsalhrfs tsrmshggfa sqstaaltrl mattdtmrdl gdqnfdflfq atllyaqitt tvardgwits ctdhyhiack sclrpieeit ldssmdytpp dvshvlktwr ngegswgqei kqiyplegnw knlapaeqsy qvgrcigfly gdlayrksth aedsslfpls iqgrirgrgf lkglldglmr asccqvihrr slahlkrpan avyggliyli dklsvsppfl sltrsgpird eletiphkip tsyptsnrdm gvivrnyfky qcrliekgky rshysqlwlf sdvlsidfig
```

```
-continued
pfsisttllq ilykpflsgk dknelrelan lssllrsgeg wedihvkfft kdillcpeei rhackfgiak dnnkdmsypp wgresrgtit tipvyytttp ypkmlemppr iqnpllsgir lgqlptgahy kirsilhgmg ihyrdflscg dgsggmtaal lrenvhsrgi fnsllelsgs vmrgaspepp saletlggdk srcvngetcw eypsdlcdpr twdyflrlka glglqidliv mdmevrdsst slkietnvrn yvhrildeqg vliyktygty iceseknavt ilgpmfktvd lvqtefsssq tsevymvckg lkklidepnp dwssineswk nlyafqsseq efarakkvst yftltgipsq fipdpfvnie tmlqifgvpt gvshaaalks sdrpadllti slfymaiisy yninhirvgp ippnppsdgi aqnvgiaitg isfwlslmek diplyqqcla viqqsfpirw eavsvkggyk qkwstrgdgl pkdtrtsdsl apignwirsl elvrnqvrln pfneilfnql crtvdnhlkw snlrrntgmi ewinrriske drsilmlksd lheenswrd
```

Alternatively, the L protein may have a sequence that is at least 70% identical to SEQ ID NO: 5 so long as it is capable of participating in the formation of the protein structure. For example, conservative substitutions of amino acids may be made without abrogating the ability of the protein to participate in the formation of the protein structure. Examples of conservative substitutions are shown in Table 1.

In some examples, the NRVP may produce functional N, P, M and G proteins after the NRVP binds and is internalized by the cell. However, the NRVP lacks the ability, or has a reduced ability, to produce functional L protein. Without functional L protein, or without the correct amount of functional L protein, new virus particles cannot be assembled.

In other examples, the NRVP may produce functional N, P, and M proteins after the NRVP binds and is internalized by the cell. However, the NRVP lacks the ability, or has a reduced ability, to produce functional G and L proteins. Without functional G and L proteins, or without the correct amounts or ratios of functional G and L proteins, new virus particles cannot be assembled.

In still other examples, the NRVP may produce functional N and P proteins after the NRVP binds and is internalized by the cell. However, the NRVP lacks the ability, or has a reduced ability, to produce functional M, G and L proteins. Without functional M, G and L proteins, or without the correct amounts or ratios of functional M, G and L proteins, new virus particles cannot be assembled.

In still other examples, the NRVP may produce functional N protein after the NRVP binds and is internalized by the cell. However, the NRVP lacks the ability, or has a reduced ability, to produce functional P, M, G and L proteins. Without functional P, M, G and L proteins, or without the correct amounts or ratios of functional P, M, G and L proteins, new virus particles cannot be assembled.

In yet other examples, the NRVP lacks the ability, or has a reduced ability, to produce functional N, P, M, G and L proteins. Without functional N, P, M, G and L proteins, or without the correct amounts or ratios of functional N, P, M, G and L proteins, new virus particles cannot be assembled.

In order for the non-replicating virus-derived particle to be able to bind the surface of a cell and be internalized, the NRVP must have sufficient number of functional G proteins on the envelope of the virus particle. It is expected that a NRVP having at least 5% of the number of G proteins found on the wild-type virus particle would still be able to bind a cell and be internalized. Preferably, the NRVP would have at least 50% of the number of G proteins found on the wild-type virus particle, and more preferably the NRVP would have at least 100% of the number of G proteins found on the wild-type virus particle. In specific examples, the NRVP has at least 60 functional G proteins per particle, at least 600 functional G proteins per particle, or at least 1200 functional G proteins per particle.

As noted above, the NRVP includes RNA having a sequence that encodes all the proteins required for new virus particle assembly. One reason that the RNA sequence may be unable to produce those proteins when the NRVP is in a cell is if the RNA is cross-linked to such an extent that protein production is reduced or stopped. In some examples, at least 0.05% cross-linked nucleotides may be sufficient to reduce or stop protein production from the RNA sequence. In other examples, the cross-linked RNA may include at least 0.5% cross-linked nucleotides. It may be preferable to have at least 1% of the nucleotides cross-linked, and more preferable to have at least 10% or at least 20% of the nucleotides cross-linked.

Cross-linking the nucleotides may increase the likelihood of rendering G-proteins unable to bind a cell surface. Accordingly, it may be preferable that less than 80% of the nucleotides be cross-linked.

The nucleotides in the RNA structure may be cross-linked to other RNA nucleotides, to amino acids in a protein in the protein structure around the RNA, or both.

In addition to the cross-linked RNA structure, the protein structure around the RNA may include a protein that has an amino acid that is: cross-linked to another protein of the protein structure; cross-linked to another amino acid of the same protein; cross-linked to the RNA structure; or any combination thereof.

Furthermore, the NRVP RNA structure may be unable to replicate by ablating the function of the NRVP RNA polymerase activity encoded by the P and L proteins. This can be effected by sufficient cross-linking of the P and L proteins to the RNA structure, by cross-linking the P and L proteins to other proteins, or by damaging NRVP protein structure such that the function of the P and L proteins are negatively affected.

Another reason that the RNA sequence may be unable to produce those proteins when the NRVP is in a cell is if the RNA structure has been cleaved to form discontinuous segments of RNA. RNA viruses, such as rhabdoviruses, have a single continuous RNA polynucleotide that includes the sequences of all of the genes that encode the proteins required for viral replication. Cleaving the single continuous polynucleotide into two or more discontinuous RNA polynucleotides results defective genome transcription, translation, or both. Proteins that are encoded on a polynucleotide without a transcription initiation site cannot be transcribed. Furthermore, the genome cannot undergo full-length replication and cannot be properly incorporated into a nascent virus particle, thereby preventing virus particle production.

NRVPs may include at least two discontinuous RNA polynucleotides, only one of which comprises a transcription initiation site. However, it may be preferable to cleave the RNA into more than two segments. Accordingly, NRVPs preferably include at least five, more preferably at least 10, and even more preferably at least 100 discontinuous RNA polynucleotides.

RNA viruses may have an RNA sequence with on the order of 11,000 nucleotides. In RNA viruses having RNA sequences with 11,000 nucleotides or more, it may be desirable to cleave the RNA into segments of no more than 10,000 nucleotides. A NRVP resulting from the cleavage of an RNA virus with 11,000 nucleotides could then have at least one RNA segment of less than 10,000 nucleotides and another RNA segment of less than 1,000 nucleotides. Since only one of the segments includes the transcription initiation site, or since the protein encoding sequence is discontinuous, the other of the segments cannot be transcribed or translated, and any proteins encoded on that segment would not be produced.

It may be preferable to cleave the RNA into smaller portions. For example, the discontinuous RNA polynucleotides may be no more than 7000, no more than 5000, no more than 3000, or no more than 1000 nucleotides.

A non-replicating virus-derived particle is produced from a live virus that includes RNA having a sequence that encodes N, P, M, G and L proteins by: optionally separating the virus-derived particle from a UV absorbing compound; and then subjecting the live virus to an RNA damaging agent to either cross-link the RNA structure, or cleave the RNA structure, thus preventing the RNA from producing sufficient proteins required for new virus particle assembly.

The RNA structure of the live virus is sufficiently cross-linked so that, when the virus-derived particle is in a cell: RNA transcription into mRNA is reduced; mRNA translation into protein is reduced; or both. Similarly, the RNA structure of the live virus is cleaved into sufficiently discontinuous RNA segments so that, when the virus-derived particle is in a cell: RNA transcription into mRNA is reduced; mRNA translation into protein is reduced; or both.

Cross-linking the RNA may be achieved by subjecting the live virus to electromagnetic radiation. The electromagnetic radiation may have a wavelength of less than about 1 mm. The energy associated with electromagnetic radiation increases as the wavelength decreases. Increased energy is associated with damage to DNA, evidenced by increased cancer rates on exposure to UV light, X-rays, and gamma radiation. Accordingly, it is preferable if the electromagnetic radiation has a wavelength of less than about 500 mm, and more preferable if the wavelength is less than about 280 nm. In particular examples, the wavelength is between about 0.1 picometers and 280 nm.

It may be especially desirable to use electromagnetic radiation having a wavelength between about 100 and about 280 nm as such a wavelength preferably induces cross-linking in nucleotides over cross-linking in proteins. When the electromagnetic radiation is in the UV spectrum, i.e. between about 100 nm and about 400 nm, the solution containing the live virus may be subjected to a dose of electromagnetic radiation between about 100 mJ/cm$^2$ and about 8,000 mJ/cm$^2$. Preferably, the dose is between about 150 mJ/cm$^2$ and about 5,000 mJ/cm$^2$. Even more preferably, the dose is between about 150 mJ/cm$^2$ and about 1,000 mJ/cm$^2$. Still even more preferably, the dose is between about 150 mJ/cm$^2$ and about 500 mJ/cm$^2$. Most preferably, the dose is between about 150 mJ/cm$^2$ and about 300 mJ/cm$^2$.

The actual dose may be dependent on the characteristics of the solution. For example, if the solution includes dyes that absorb UV light, then a greater dose is required. Similarly, if the solution is irradiated from a single point and the container is large, there may be live virus that is not exposed to the full intensity of the UV light. In such a situation, a greater dose or stirring the solution may be beneficial. A skilled person would be able to determine the parameters necessary for providing an appropriate dose.

In situations where the media holding the live virus is turbid, includes dye, or otherwise absorbs UV light, it may be desirable to irradiate the live virus with x-rays (i.e. electromagnetic radiation having a wavelength between 0.01 and 10 nm) or gamma rays (i.e. electromagnetic radiation having a wavelength less than 10 picometers). When the electromagnetic radiation is gamma irradiation, the live virus may be subjected to a dose between about 1 kGy and about 50 kGy. More preferably, the dose is between about 5 kGy and about 20 kGy. The gamma radiation may be generated from cobalt-60.

The live virus may be subjected to the electromagnetic radiation at a temperature of 4° C. or lower. For example, the live virus may be subjected to UV radiation at a temperature of about 4° C. In another example, the live virus may be subjected to gamma radiation at a temperature of about −80° C. In yet another example, the live virus may be subjected to gamma radiation at a temperature of about −130° C.

As noted above, the RNA structure may be cross-linked, or cleaved into sufficiently discontinuous RNA segments, to reduce or prevent RNA transcription into mRNA; mRNA translation into protein; or both. In addition to the electromagnetic radiation discussed above, this may be achieved by exposing the live virus to a chemical agent, such as an alkylating agent capable of crosslinking RNA, or a free radical forming agent capable of cleaving RNA. Examples of such cross-linking agents include busulfan, cyclophosphamide, melphalan, formaldehyde, carbodiimide and bis-sulfosuccinimidyl suberate. Examples of free radical forming agents include peroxides, hydrogen bromine, ammonium persulfate and hydroxyl radical.

The live virus may be separated from a UV-absorbing compound by fractionating the growth medium used to generate the viral particles. The growth medium maybe fractionated, for example, in a sucrose gradient. Once the NRVP has been prepared, the NRVP may be separated by fractionating or filtering the diluent containing the virus-derived particles. The diluent may be fractionated, for example, in a sucrose gradient or filtered by tangential flow filtration.

The present disclosure also includes a method of stimulating an immune response by administering non-replicating virus-derived particles as described above to a patient. The administration of the NRVPs induces expression and release of cytokines in the patient. Exemplary cytokines which may be released in the patient include: interleukins, interferons, inflammatory cytokines, members of the CXC chemokine family, members of the tumor necrosis factor family, or any combination thereof. These factors can result in the presentation or recognition of tumor antigens.

The disclosure also includes a method of inducing cell death of cancerous cells in a patient. The method includes administering non-replicating virus-derived particles as described above to the patient.

The disclosure further includes a method of preferentially inducing cell death in cancerous cells or non-cancerous cells. The method includes administering non-replicating virus-derived particles as described above to the patient.

The cell death may be through apoptosis, for example caused by the presence of the NRVPs, or constituents of the NRVPs, in the cell. Alternatively, the cell death may be due to recruitment of innate immune effector cells, adaptive immune effector cells, or any combination thereof, for example caused by cytokines released by the cell. The adaptive immune effector cells may be T-cells, B-cells, or both. The innate immune effector cells may include mast cells, phagocytes (such as macrophages, neutrophils, or dendritic cells), basophils, eosinophils, natural killer cells, γδ T cells, or any combination thereof.

The patient is treated with sufficient numbers of NRVPs to stimulate the immune response or induce cell death of cancerous cells. Since the NRVPs do not form live virus particles, it is desirable to administer the NRVPs in an amount that is greater than treatments with replication competent viruses. The patient may be administered with 1E10 to 1E15 non-replicating virus-derived particles, though in preferred examples the patient is administered with 1E11 to 1E13 non-replicating virus-derived particles.

There may be a synergistic benefit when combining treatment of a patient with NRVPs and treatment with a chemotherapeutic agent. The chemotherapeutic may be, for example: bendamustine, dexamethasone, doxorubicin, vincristine, imatinib, disatinib or idarubicin. These agents may improve sensitivity to NRVP-mediated apoptosis, enhance cytokine secretion, improve anti-tumor immune responses, promote vascular shutdown, or any combination thereof.

NRVPs may be used to treat solid tumors or non-solid tumors, such as leukemia. However, since NRVPs do not form live virus particles in a cell, it is especially desirable to expose all cancer cells to the injected NRVPs. This is in contrast to administration of replication competent viruses, where exposure of a portion of the cancer cells to the injected virus results in production of additional virus and subsequent exposure of the remaining cancer cells to the generated virus particles.

In view of the lack of production of virus particles, it is preferable to use NRVPs to treat leukemia since intravenous administration of the NRVPs results in a substantial fraction of the leukemic cells being exposed to the particles. In contrast, with solid tumors, a portion of the cells in the solid tumor may not be exposed to the injected NRVPs. The mode of administration of the non-replicating virus-derived particles may be determined by the cancer to be treated. The NRVPs may be administered to the patient intratumorally, intranasally, intramuscularly, intradermally, intraperitoneally, intra-arterially, intravenously, subcutaneously or intracranially.

Non-replicating virus-derived particles (NRVPs) of the present disclosure may be formed from wild type Rhabdovirus particles modified so as to lack the ability to spread between cells. The non-replicating Rhabdovirus-derived particle may be derived from a replication competent wild type Rhabdovirus particle. Once modified, the NRRP cannot sustain virion replication. NRRPs may retain cytolytic tropism against immortalized cells. Specific examples of NRRPs have innate and/or adaptive immune-stimulating properties against immortalized cells.

For the purposes of the present disclosure, the expression "immortalized cells" means cells with unchecked cell division, and includes, without limitation, hyperproliferative cells, tumor or cancer cells and transformed immortalized cells. Hyperproliferative cell(s) refer to any neoplasm or any chronically infected cell or tissue. The neoplasm can be, for instance, any benign neoplasm, cystic neoplasm, carcinoma in situ, malignant neoplasm, metastatic neoplasm, or secondary neoplasm. The hyperproliferative cell may be a hematopoietic cancer cell or a cell from a solid tumor.

NRRPs according to the present disclosure may retain cytolytic tropism against immortalized cells. This means that NRRPs will induce cell death preferentially in immortalized cells such as tumor or cancer cells and transformed immortalized cells.

The wild type Rhabdovirus may be modified to generate the NRRP by a means that disrupts its genome replication and/or expression. This means that genome replication and/or expression is decreased over parental baseline expression. Genome expression could also be ablated.

To disrupt genome expression of the wild type Rhabdovirus, electromagnetic (EM) irradiation can be used. Electromagnetic irradiation may include UV irradiation, infrared, X-ray, gamma and other types of irradiation in the EM spectrum such as UVC (200-280 nanometer). Chemical-induced disruption can also be used to disrupt genome expression of the wild type Rhabdovirus. For example, a genome-damaging agent such as busulfan can be used.

The EM dose required to sufficiently disrupt genome expression of the wild type Rhabdovirus will be method dependent, and will vary according to parameters such as virus concentration, turbidity of the virus stock preparation, volume used, the presence of contaminants or purity of the virus stock preparation, the diluent used, and the receptacle in which the virus preparation is stored for the procedure (plastic, glass, etc.). Chemical dosing may also be affected by various parameters.

In one example, 50 μl of a 1E10 PFU/ml stock of the wild type Rhabdoviruses purified using the sucrose cushion method was irradiated at 250 mJ/cm$^2$ (for about 40 seconds).

The present disclosure further provides a non-replicating Rhabdovirus-derived particle that has been made from a wild type Rhabdovirus-derived particle. The wild type virus has been modified to lack the ability to spread between cells but to retain innate and/or adaptive immune-stimulating properties.

The present disclosure also provides for a use of a NRVP, and specifically a NRRP, to treat a population of immortalized cells.

For the purposes of the present disclosure, "treat" would be understood to mean applications where the NRVP or NRRP is used alone or in combination with radiation therapies, chemotherapies, immuno-therapies, surgery, oncolytic virus-based therapies or other virus-based therapies.

A person skilled in the art will understand that "chemotherapies" includes, but is not limited to, therapies involving the use of mitotic inhibitors, IMiDS such as lenalidomide or pomalidomide, chromatin modifying agents, HDAC inhibitors such as SAHA, hypomethylating agents, alkylating agents, mTOR inhibitors, tyrosine kinase inhibitors, proteasome inhibitors, antimetabolites, DNA damaging or DNA regulating agents, phosphodiesterase inhibitors, SMAC mimetics such as LCL161, corticosteroids and cytokine/chemokines.

For example, chemotherapy would include therapies that use: alkylating agents, DNA damaging agents or DNA regulating agents, mitotic inhibitors, tyrosine kinase inhibitors, proteasome inhibitors, IMiDS, antimetabolites, mTOR inhibitors, chromatin modifying agents, HDAC inhibitors, hypomethylating agents, phosphodiesterase inhibitors, corticosteroids and cytokines/chemokines. Specific chemotherapies include, but are not limited to; bendamustine, busulfan, carboplatin, carmustine, chlorambucil, cisplatin, cyclophosphamide, dacarbazine, lomustine, melphalan, temozolomide, thiotepa, oxaliplatin, procarbazine, pentostatin, cladribine, clofarabine, cytarabine, fludarabine, gemcitabine, hydroxyurea, mercaptopurine, nelarabine, fluorouracil, bleomycin, dactinomycin, daunorubicin, doxorubicin, doxorubicin liposomal, idarubicin, mitoxantrone, capecitabine, topotecan, irinotecan, etoposide, paclitaxel, teniposide, thioguanine, omacetaxin, altretamine, asparaginase, asparaginase, pegaspargase, Isotretinoin, retinoic acid, arsenic, vinblastine, vincristine, vincristine liposomal, bosutinib, dasatinib, imatinib, nilotinib, sunitinib, vemurafenib, regorafenib, bortezomib, carfilzomib, thalidomide, lenalidomide, pomalidomide, methotrexate, pralatrexate, everolimus, Temsirolimus, vorinostat, romidepsin, valproic acid, decitabine, azacitidine, anagrelide, cortisone, dexamethasone, prednisone and triamcinolone, interferon alfa 2a, interferon alfa 2b, peginterferon alfa 2b, interferon beta 1b, aldesleukin/IL-2, denileukin diftitox, granulocyte colony stimulating factor and granulocyte macrophage colony stimulating factor.

For the purposes of the present disclosure, the term "immunotherapies" shall mean immunotherapies targeting CD20 (such as rituximab, Ibritumomabtiuxetan and tositumomab), CD47, CD33, CD38, CD138, CS1, CD52 (such as alemtuzimab), VEGF (such as bevacizumab), Her2/Neu (such as Trastuzumab), EGFR (such as cetuximab and nimotuzumab), CTLA4 (such as ipilimumab) or IGF-1 (such as ganitumab). Other immunotherapies known to a person skilled in the art may also be included within the scope of the term "immuno-therapies".

The reference to "oncolytic virus-based therapies" includes those known in the art, including Pox virus-based therapies (Vaccinia-based viruses), Herpes Simplex Virus-based therapies (OncoVEXGM-CSF), Rhabdovirus-based therapies (MG1, VSV-IFNb, VSVd51), Reovirus (Reolysin), Adenovirus-based therapies (ONYX 015), Measles virus-based therapies, New Castle Disease virus-based therapies, Alpha virus-based therapies, and Parvovirus species-based therapies.

NRVPs and NRRPs can be administered intratumorally, intranasally, intramuscularly, intradermally, intraperitoneally, intra-arterially, intravenously, subcutaneously or intracranially.

The oncolytic properties of NRRPs in several different in-vitro and in-vivo models using two different Rhabdovirus-derived strains and several different cell types including patient samples were demonstrated, as discussed in greater detail below.

Tumor specific cytotoxicity was characterized in a number of assays including microscopy characterization of cellular phenotype, resazurin cytotoxicity quantification, and flow cytometry of tumor cell killing.

Using an immune-protection model against L1210 indicates that NRRP activation of programmed cell death pathways leads to the generation of innate and adaptive immune response against the tumor. As such, treatment with NRRPs does not require each cell to become infected to maintain efficacy, and therefore may be used as a treatment alone or as an adjuvant in an anticancer therapeutic regimens.

Luminex-based quantification of cytokines induced by NRRPs in L1210 bearing mice during acute blast crisis was also performed. All identified cytokines were induced over 2 fold by NRRP-treated mice and are statistically significant (non-paired t-test pV<0.05). pV has been corrected to account for multiple hypothesis testing (Benjamini & Hochberg Method).

This experiment also shows that NRRPs may be optimally effective when applied at a high NRRP to cell ratio (i.e., >1). This higher dosing ensures that the majority of cells within a cell population encounter a cytotoxic NRRP. This contrasts live OV therapies, which rely on viral spread to hopefully achieve therapeutic efficacy, and inherently utilize a low OV to cell ratio to promote safe delivery to the recipient.

EXAMPLES

For all figures except FIG. 1A, NRRPs were generated by UVC-irradiation at a dose of 250 mJ/cm$^2$ of a 50 µl sample of 1E10 PFU/ml of live VSV-GFP, purified using a sucrose cushion method where the virus preparation was centrifuged through a 20% (w/v) sucrose cushion in water (5 ml) at 148,000×g for 120 minutes.

Example 1

VSV-Based NRRPs Generated by Irradiation with Electromagnetic Radiation

Figure 1B:
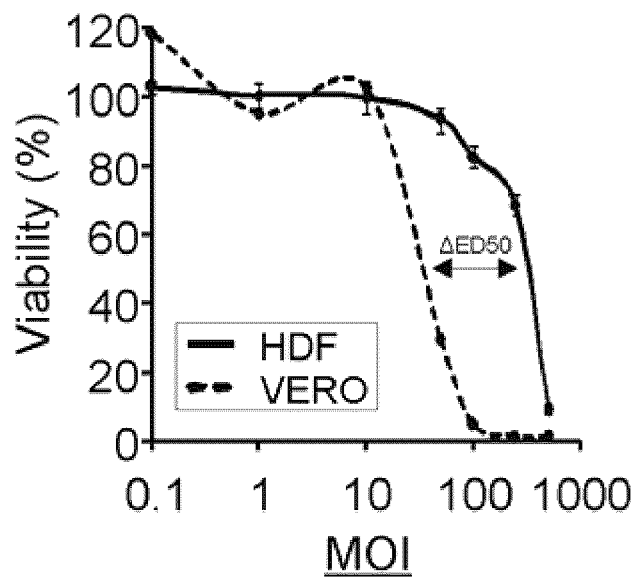
FIG. 1B is a graph showing the impact of MOI on the cytotoxicity induced by NRRPs in Vero and HDFN cells as illustrated by the viability as a function MOI. Viability was quantified using the resazurin assay 72 h post infection. Error bars represent the standard deviation between triplicate experiments.
Figure 2A:
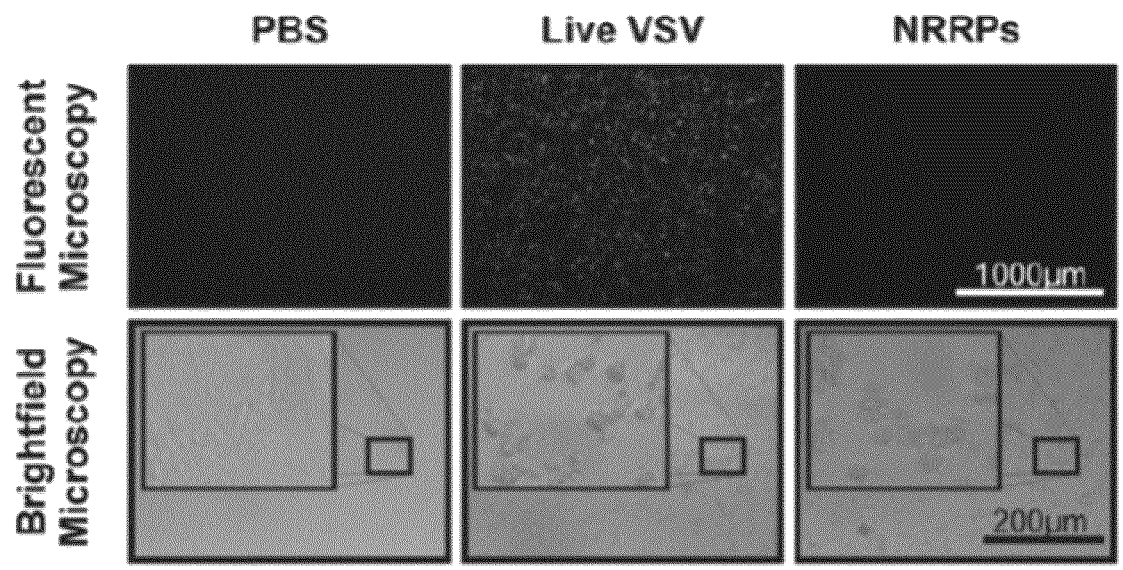
FIG. 2A is a set of images show the cytotoxicity of NRRPs in Vero immortalized cells through fluorescent and brightfield microscopy images of Vero cells treated with PBS, Live VSV-GFP or NRRPs taken at 24 and 72 hours post-infection or post-treatment. The multiplicity of infection (MOI) used in these experiments was set at 100 particles per cell.
Figure 2B:
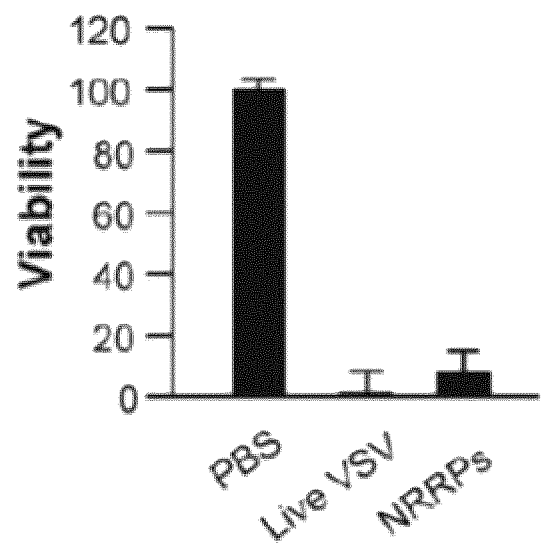
FIG. 2B is a graph showing the cytotoxicity of NRRPs through resazurin quantification of cellular viability 72 h post treatment. Error bars represent the standard deviation between triplicate experiments.
Figure 2C:
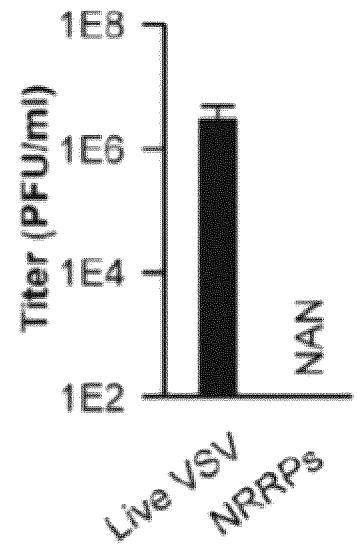
FIG. 2C is a graph showing viral titers produced. NAN means "not as a number" as no virions were detected.

UV photonic damage of rhabdoviruses may be used to generate a non-replicating virus-derived particle that retained bioactivity. Using high-dose UV irradiation ablates the rhabdoviruses's genome, rendering the virus biologically inert. However, it has now been discovered that UV irradiation may be applied at a dose that still allows the virus to bind and be internalized by a cell, but stops, or substantially reduces, the ability of the particle to form new virus particles when the virus particle is in the cell. Accordingly, virus replication is lost, yet biological activities are maintained.

It was determined that irradiation of purified VSV (a Rhabdovirus) expressing green fluorescent protein with a dose between about 100 and about 1000 mJ/cm$^2$ dose of UV fluence generates a NRRP that retains cytolytic tropism against immortalized cells (FIGS. 1A and 1B), but that lacks the ability to spread between cells (FIG. 2A).

A 250 mJ/cm$^2$ dose of UV irradiation was applied to the wild type strain of VSV to generate VSV-based NRRPs according to the present disclosure. In FIG. 1A, the UV dose 1E2 corresponds to 100 mJ/cm$^2$. As such, when irradiated at a dose of 250 mJ/cm$^2$), VSV-eGFP lost its expression capabilities, yet maintained potent cytotoxicity against the immortalized production cell line (Vero) (FIG. 2B). Tittering of the virus following infection confirmed that the resulting particle was unable to replicate in these cells in sharp contrast with live virus infection (FIG. 2C). This effect was equally observed when using other members of the Rhabdovirus family, including Maraba (FIGS. 3A, 3B and 3C).

Dose response curves, shown in FIG. 1A, indicate that cytotoxicity is reduced at UV doses above 1000 mJ/cm$^2$ and completely abrogated at a UV dose of 10,000 mJ/cm$^2$. It is believed that cytotoxicity is abrogated at this dose because the G proteins are cross-linked to such an extent that they are unable to allow the treated virus to bind the cell surface and/or be internalized by the cell. By comparing and contrasting with normal neonatal human dermal fibroblats (HDF) (FIGS. 1A and 1B), it appears that cytotoxicity is preferential to cancerous cells over non-cancerous cells. Indeed, non-cancerous cells appear to require around 10 times more virus to become sensitive to NRRP-mediated cytotoxicity (FIG. 1B).

To confirm the absence of NRRP replication and spread in acute leukemia cells, GFP synthesis and viral titers were quantified following in-vitro treatment of an aggressive murine acute lymphoblastic leukemia cell line (L1210), alongside the Vero control cell line (normal kidney epithelial cells). In both treated cell lines, no detectable live virus was observed (FIGS. 4A and 4B).

Western blot analysis of the viral genome indicates that the NRRPs have a reduced global genome expression (FIG. 5). UV-doses which block virion production and decrease genome expression are associated with distinct oncolytic activity. In these experiments, a high (greater than or equal to 1) multiplicity of infection (MOI), or particle to cell ratio, may be used to ensure that each tumor cell encounters a NRRP and induces extensive cell death across the population (FIG. 1B).

Example 2

VSV-Based NRRPs Generated by Exposure to an RNA Alkylating Agent

Figure 6A:
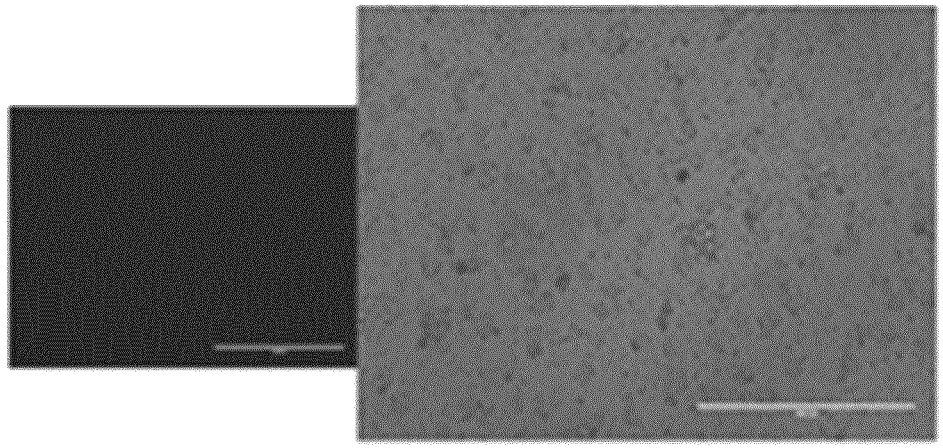
FIG. 6A is a set of fluorescent and brightfield images of Vero cells treated with chemically-generated, or busulfan-generated, NRRPs.
Figure 6B:
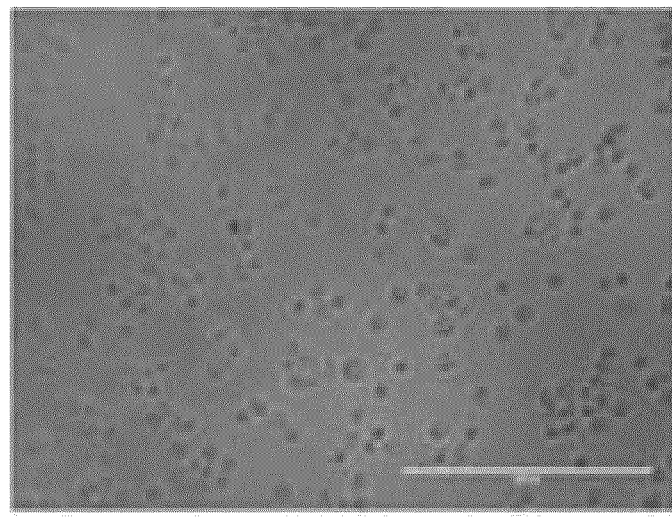
FIG. 6B is a brightfield microscopy image of Vero cells treated with busulfan alone, at the same dose used to generate NRRPs in FIG. 6A, for 15 hours.
Figure 6C:
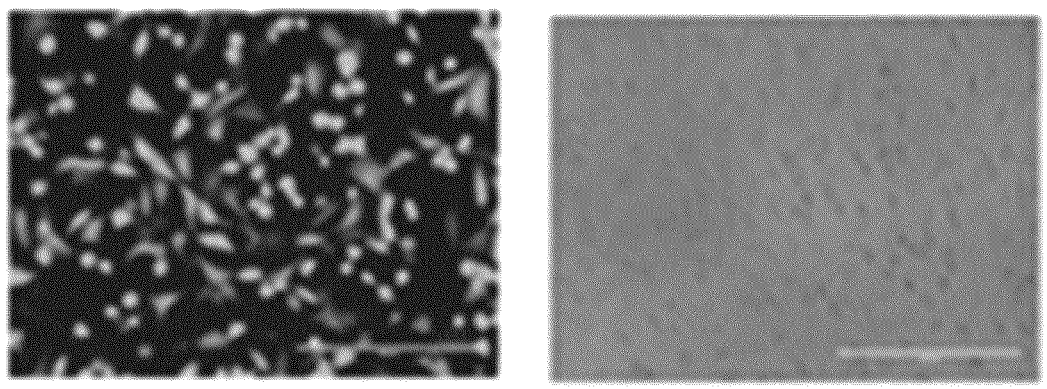
FIG. 6C is a set of fluorescent and brightfield images of Vero cells treated with Live VSV-GFP.

In another example, NRRPs were chemically generated by treating VSV with 6 mg/mL of busulfan at 4° C. for 24 hours and added to Vero cells for 24 hours. Less than 4% of the Vero cells remained viable after treatment (FIG. 6A). This effect was attributable to the NRRPs since treatment with busulfan alone for 24 hours showed that Vero cells remained around 82% viable (FIG. 6B). FIG. 6C shows cytopathic effect of live VSV-GFP infected Vero cells at 24 hours and that this live virus stock (VSV-GFP), from which the NRRPs were derived, was indeed replication competent—by evidence of GFP expression.

Example 3

VSV-Based NRRPs Generated by Exposure to Gamma Radiation

Figure 7A:
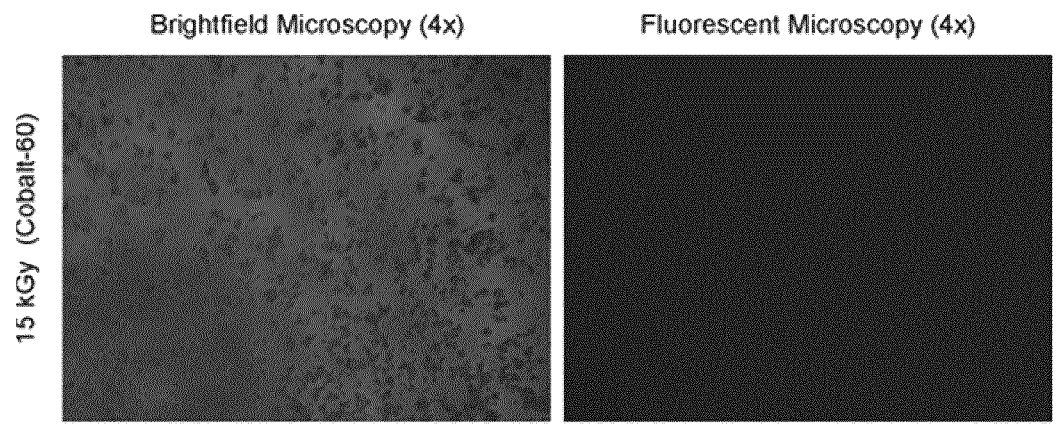
FIG. 7A is a set of brightfield and fluorescent images of Vero cells treated with NRRPs, generated by taking 1E10 frozen wild type VSV and irradiating this preparation with 15 kGy Cobalt-60.
Figure 7B:
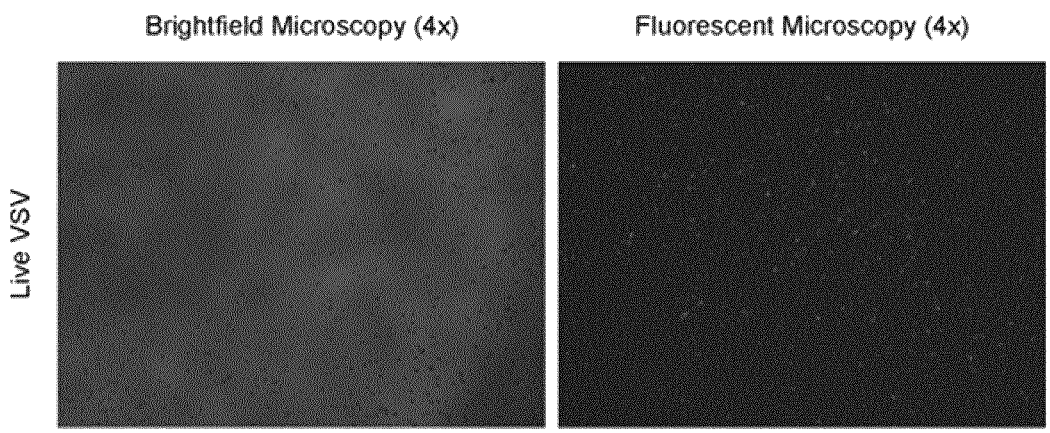
FIG. 7B is a set of brightfield and fluorescent images of Vero cells treated with live wild type VSV-GFP.
Figure 7C:
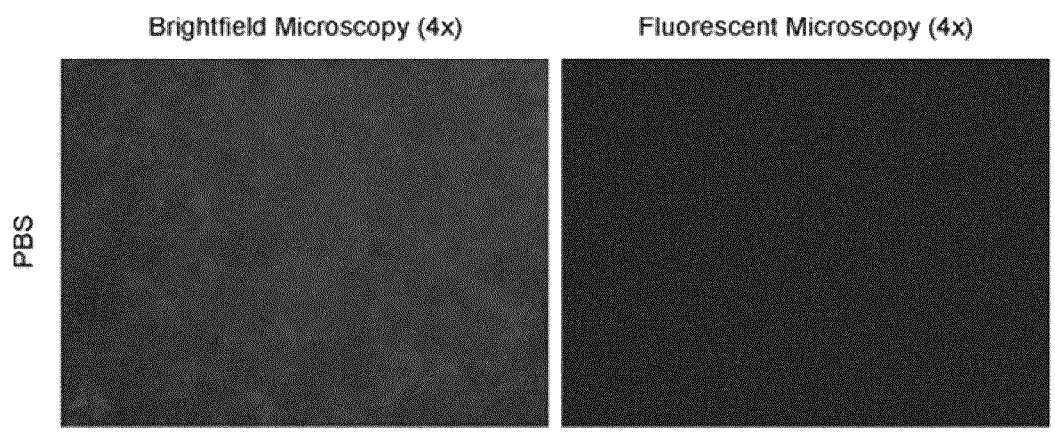
FIG. 7C is a set of brightfield and fluorescent images of Vero cells in PBS.

In yet another example, NRRPs were generated by irradiating 1E10 frozen VSV with 15 kGy Cobalt-60 at –80° C. and 1000 particles per cell were added to Vero cells for 48 hours. Again, the cytopathic effect of NRRPs was clearly evident on these immortalized cells (FIG. 7A). The NRRP-induced morphological effects of cellular apoptosis and death compare to the cytopathic effects of treating the same cells with live VSV-GFP, over the same time period of 48 hours (FIG. 7B). Vero cells treated with PBS alone remained fully viable, without cytopathic effects and showed no fluorescence (FIG. 7C).

Example 4

NRRPS are an Efficient Treatment Against Leukemia Cells In Vitro

Figure 3A:
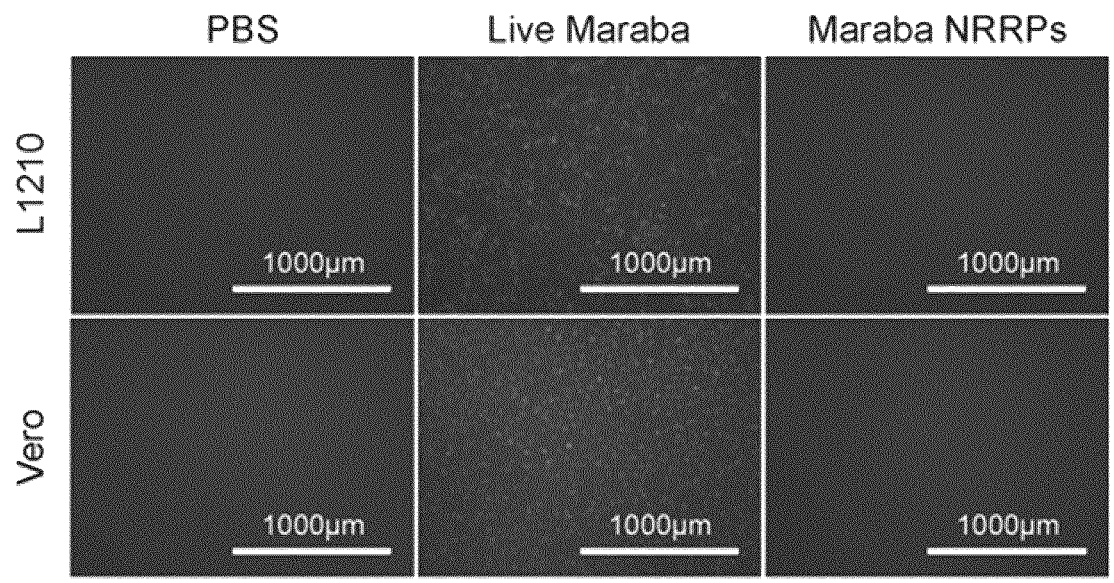
FIG. 3A is a set of fluorescent microscopy images (4×) of leukemic (L1210) and Vero cells treated with PBS, Live Maraba virus, and Maraba virus-derived NRRPs. Images were taken at 24 h post treatment.
Figure 3B:
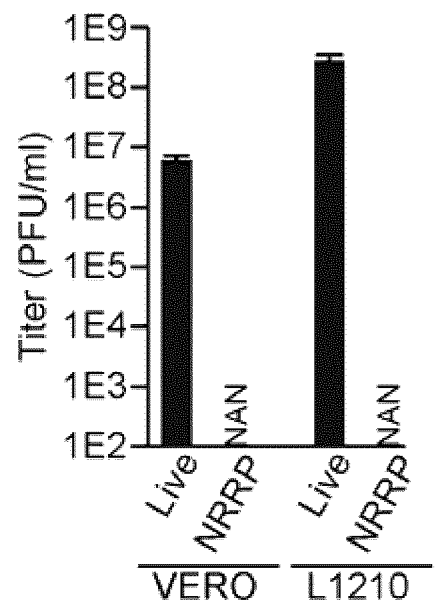
FIG. 3B is a graph showing viral titers obtained from tumor cells.
Figure 3C:
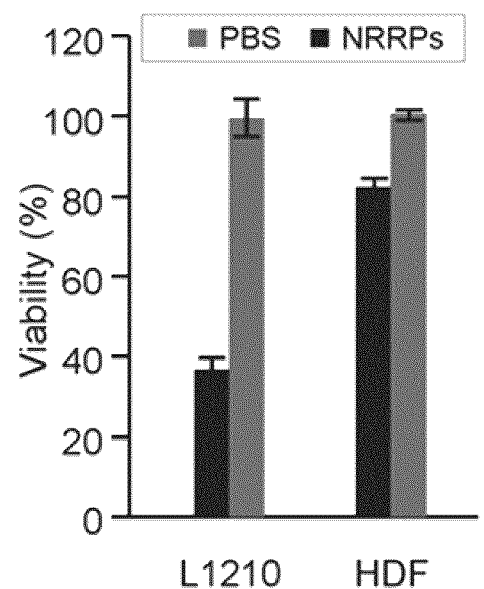
FIG. 3C is a graph showing resazurin quantification of cellular viability of L1210 leukemia cells and HDF normal cells, 72 h post infection.
Figure 4A:
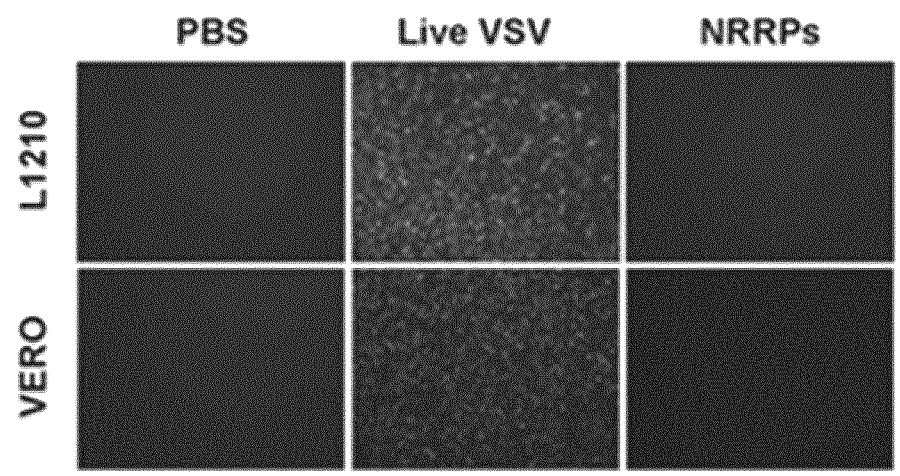
FIG. 4A is a set of images showing fluorescent images of L1210 and Vero cells treated with PBS, Live VSV-GFP, or NRRPs.
Figure 4B:
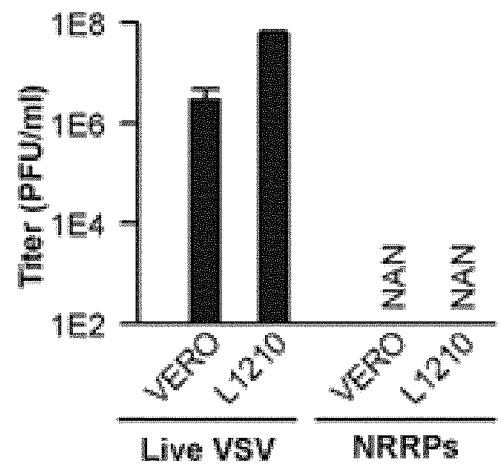
FIG. 4B is a graph showing the viral titers generated from L1210 acute leukemia and Vero immortalized cells
Figure 5:
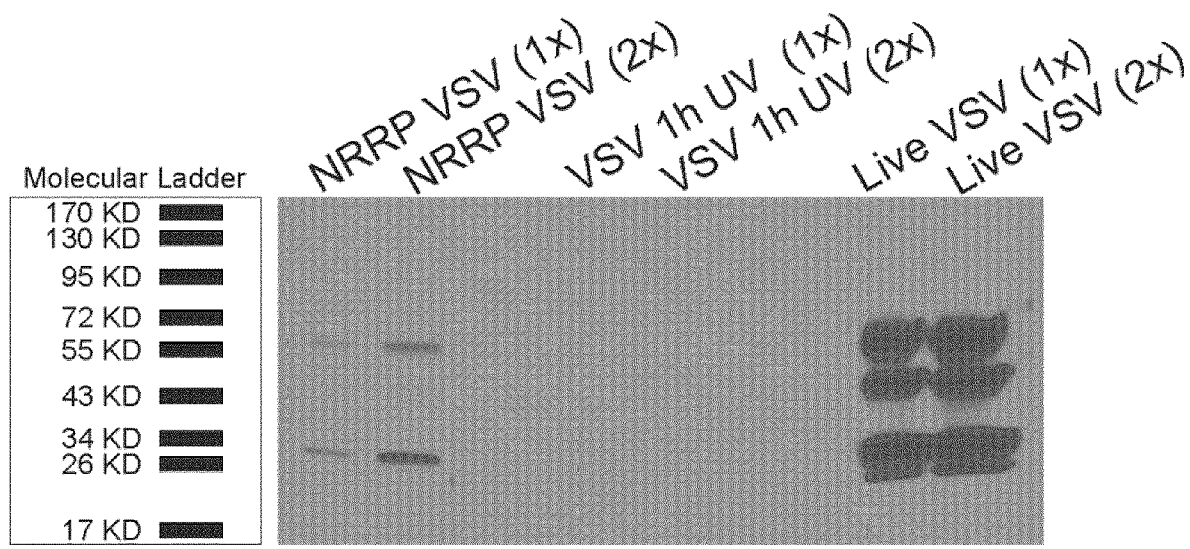
FIG. 5 is an image of a Western blot of NRRP genome expression compared to the genome expression of a virus exposed to a UV dose of 20,000 mJ/cm$^2$, where loss of cytotoxicity was observed, and a live virus as a control. Reference to 1× or 2× refers to the amount of protein loaded onto the gel. Proteins were extracted 15 h post infection.
Figure 8A:
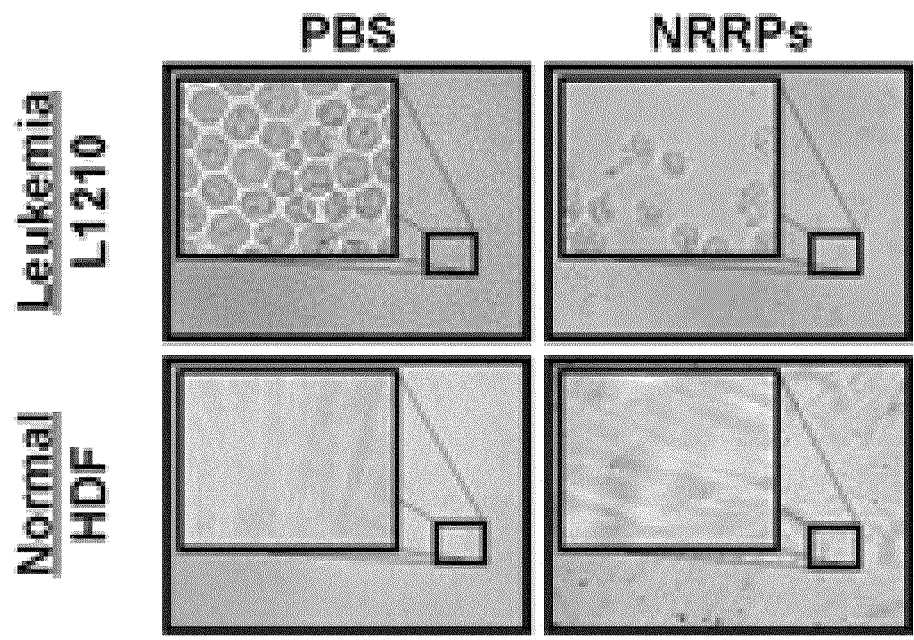
FIG. 8A is a set of brightfield images of L1210 and HDF cells treated with PBS or NRRPs at an MOI of 100.
Figure 8B:
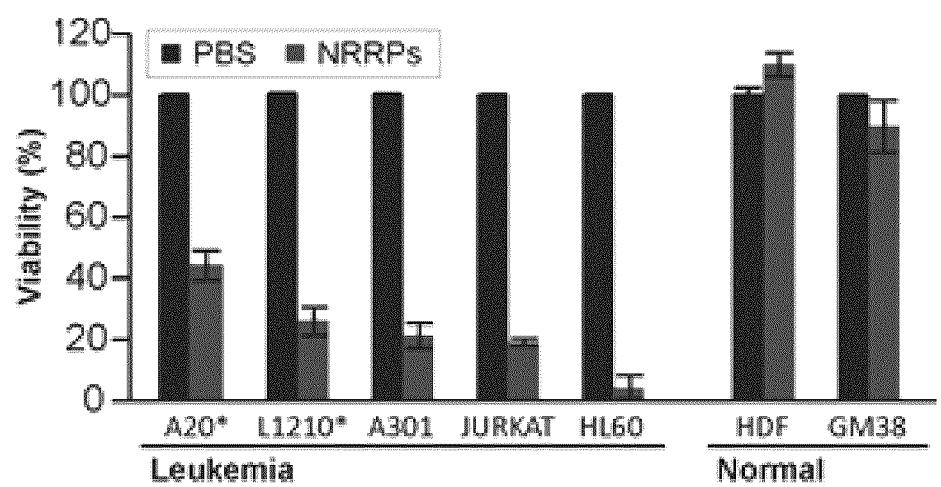
FIG. 8B is a graph showing resazurin quantification of viability in leukemia and normal cell lines. Murine cell lines are denoted by *.
Figure 8C:
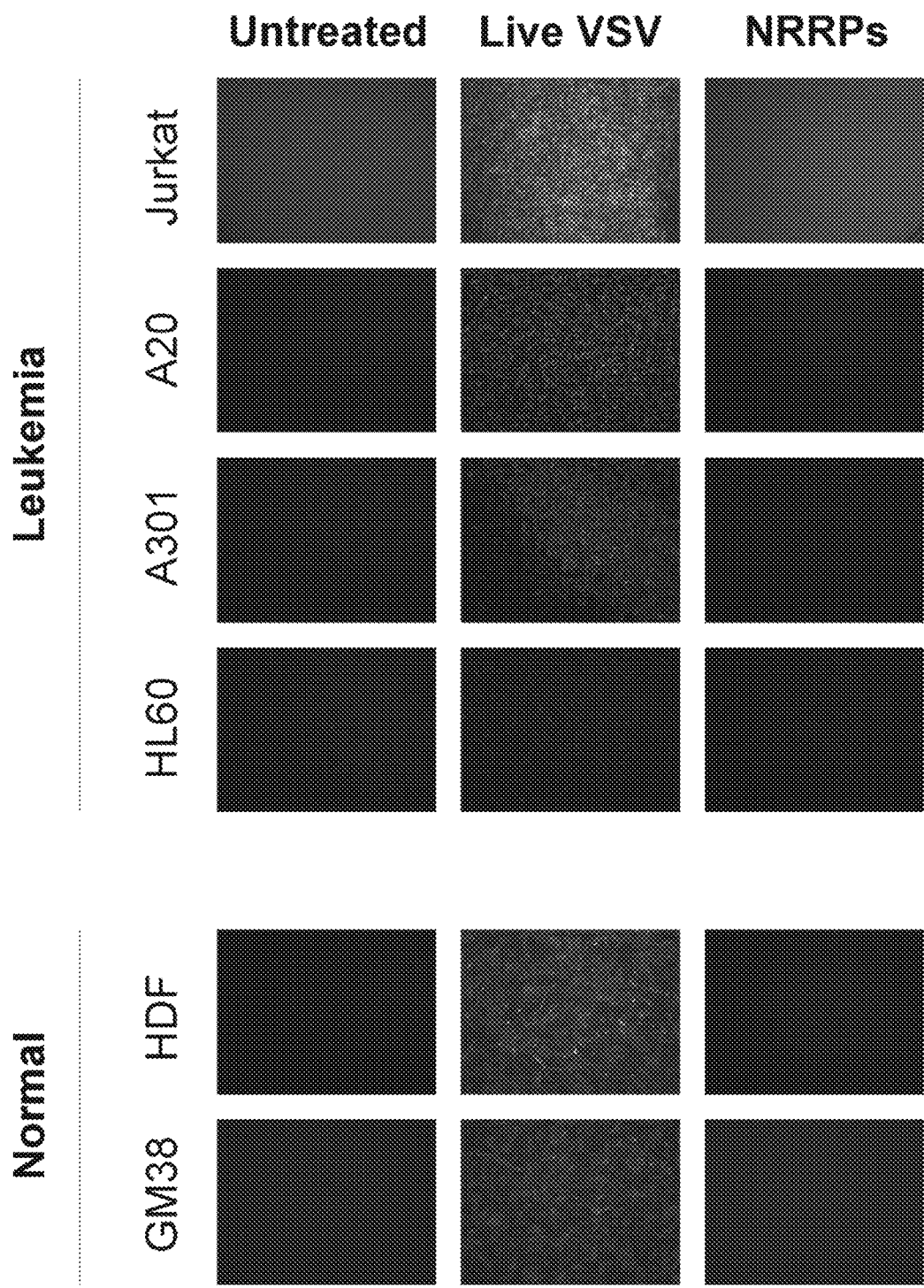
FIG. 8C is a set of fluorescent microscopy images of PBS, live VSV-GFP, or NRRP treatment in murine human Jurkat T-cell acute leukemia, murine A20 B-cell lymphoblastic leukemia, A301 T-cell lymphoblastic leukemia, and HL60 acute promyelocytic leukemia and GM38 and HDF normal cell lines.

Whether acute leukemia cells are susceptible to NRRP-mediated cell death was examined with VSV-based NRRPs generated by the UV method. First, the cytotoxicity induced in the L1210 cell line and that observed in normal Human Dermal Fibroblasts (HDF) was determined. While both cell lines were susceptible to live virus infection, NRRPs exclusively induced death in leukemic L1210 cells (FIG. 8A). The classic apoptotic phenotype, characterized by a reduced cell diameter, a "shriveled" appearance with numerous apoptotic bodies and fragmented nuclear content, was observed in acute leukemia L1210 cells. Cytotoxicity was quantified using a standard resazurin assay in several human and murine cell lines. In these experiments, acute leukemias were highly susceptible to NRRP-mediated cell death while preserving the viability of normal cells (FIG. 8B). Similar results were determined using Maraba-based NRRPs, an alternative Rhabdovirus strain (FIGS. 3A and 3B). The absence of genome expression was confirmed by fluorescence microscopy (FIG. 8C).

Figure 9:
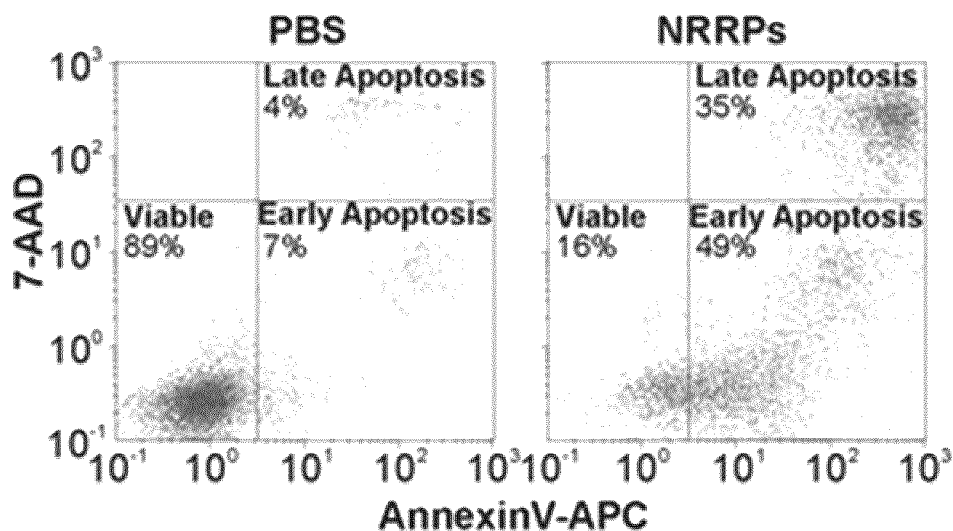
FIG. 9 is a set of graphs showing the flow cytometry analysis of Annexin V-APC and 7-AAD staining in L1210 cells treated with PBS or NRRPs.

The level of apoptosis in L1210 cell lines was quantified by flow cytometry. Thirty hours post treatment, NRRPs induced extensive (84% of population) early/late apoptosis (FIG. 9). VSV-induced apoptosis has been shown to directly correlate with the level of endoplasmic reticulum (ER) stress present (10). Interestingly, when the cell's capacity to mitigate ER stress is breached, immunogenic apoptosis can be induced (16). NRRPs induce this unique form of cellular death as described later.

Figure 10:
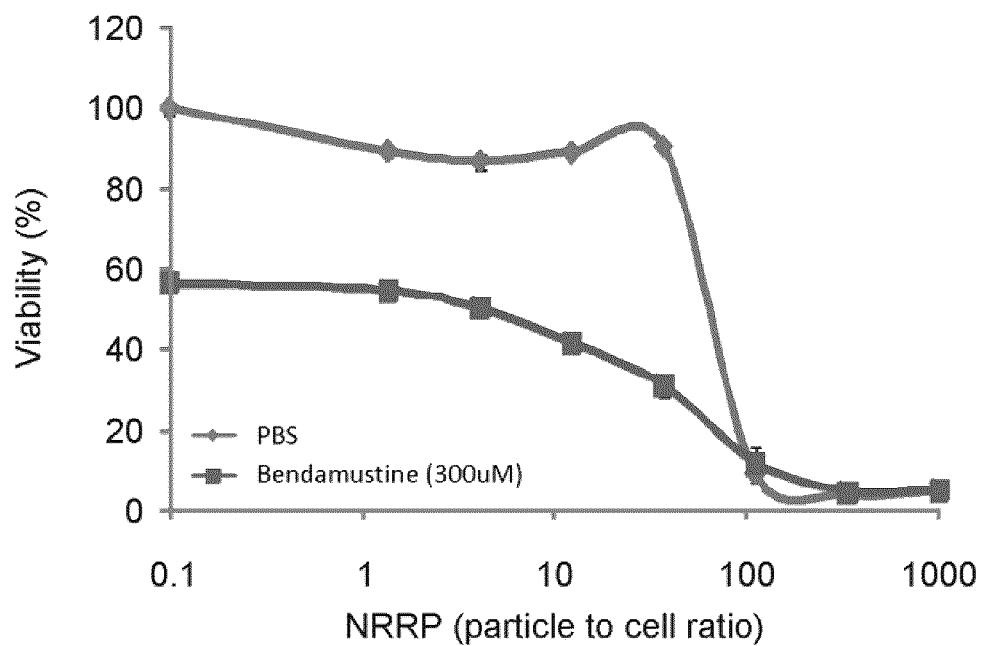
FIG. 10 is a graph illustrating cell viability following a resazurin quantification assay for L1210 acute leukemia cell line taken 72 hours post treatment with UV-generated NRRPs and the combinatorial effect of UV-generated NRRPs with bendamustine (300 μM).
Figure 11:
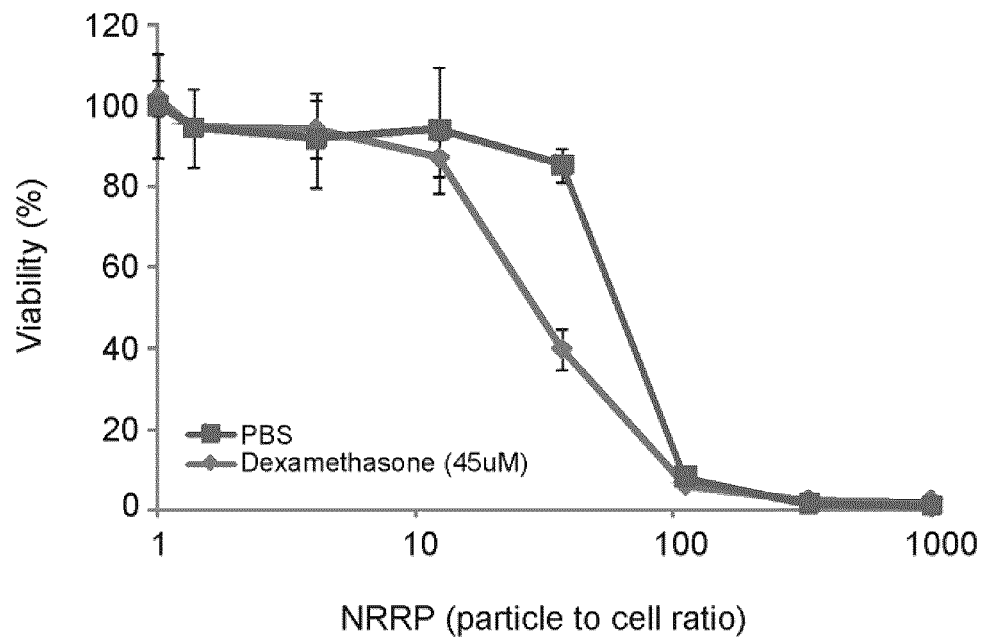
FIG. 11 is a graph illustrating cell viability following a resazurin quantification assay for L1210 acute leukemia cell line taken 72 hours post treatment with UV-generated NRRPs and the combinatorial effect of UV-generated NRRPs with dexamethasone (45 μM).
Figure 12:
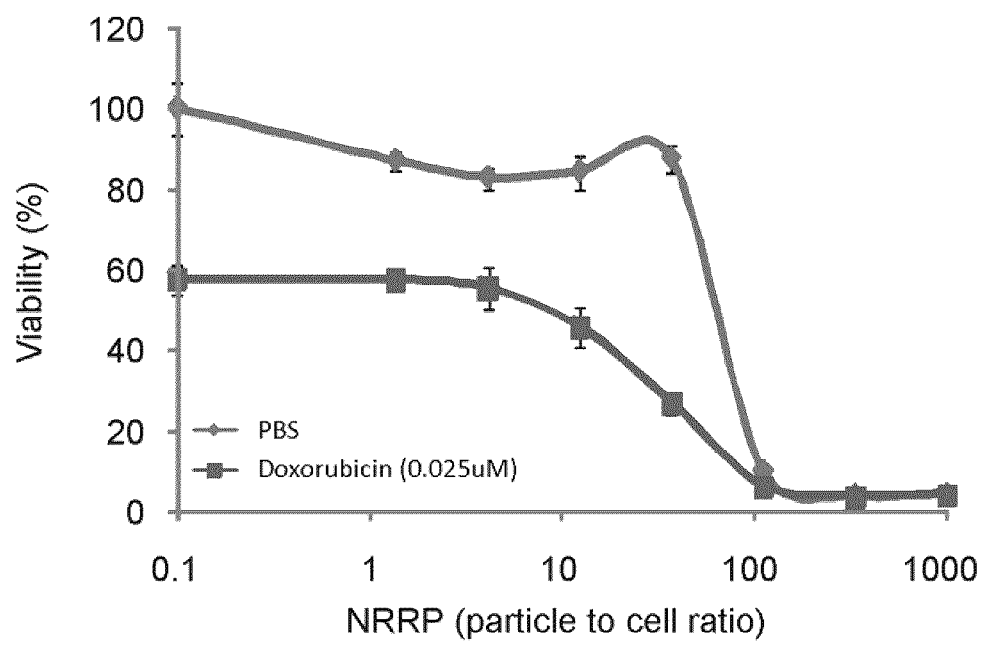
FIG. 12 is a graph illustrating cell viability following a resazurin quantification assay for L1210 acute leukemia cell line taken 72 hours post treatment with UV-generated NRRPs and the combinatorial effect of UV-generated NRRPs with doxorubicin (0.025 μM).
Figure 13:
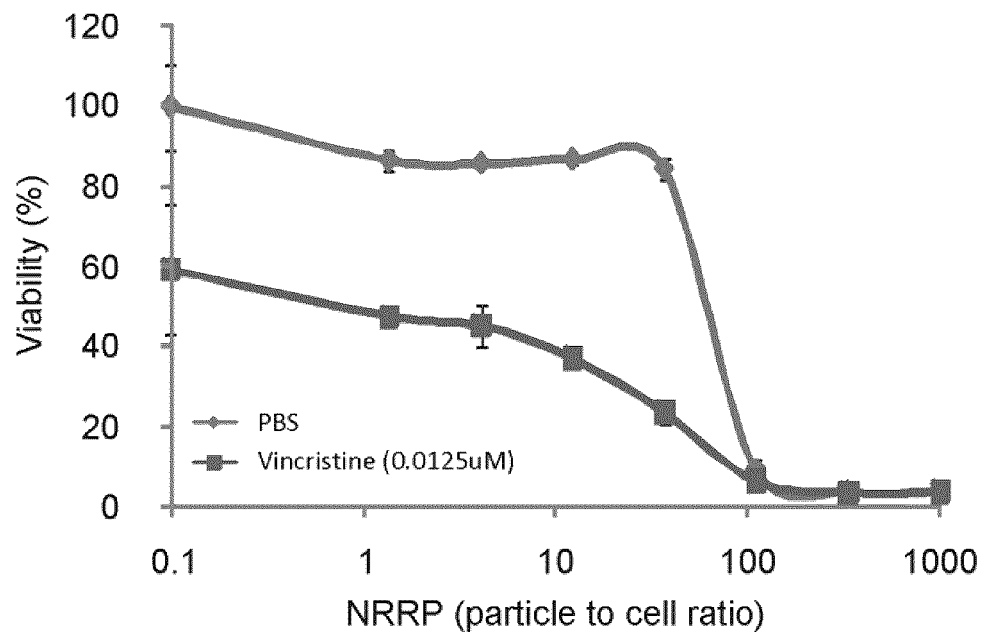
FIG. 13 is a graph illustrating cell viability following a resazurin quantification assay for L1210 acute leukemia cell line taken 72 hours post treatment with UV-generated NRRPs and the combinatorial effect of UV-generated NRRPs with vincristine (0.0125 μM).

In other examples, L1210 leukemia cells were treated with NRRPs in combination with either 300 µM bendamustine (FIG. 10); 45 µM dexamethasone (FIG. 11); 0.025 µM doxorubicin (FIG. 12) or 0.0125 µM vincristine (FIG. 13) for 72 hours. NRRPs are shown to induce cytotoxic effect on their own in the usual manner however in combination with the above drugs additional and/or synergistic cytotoxic effect is observed. This demonstrates that a unique therapeutic potentiation-effect occurs when NRRP-therapy is combined with other chemotherapeutics/pharmacologics.

Figure 14:
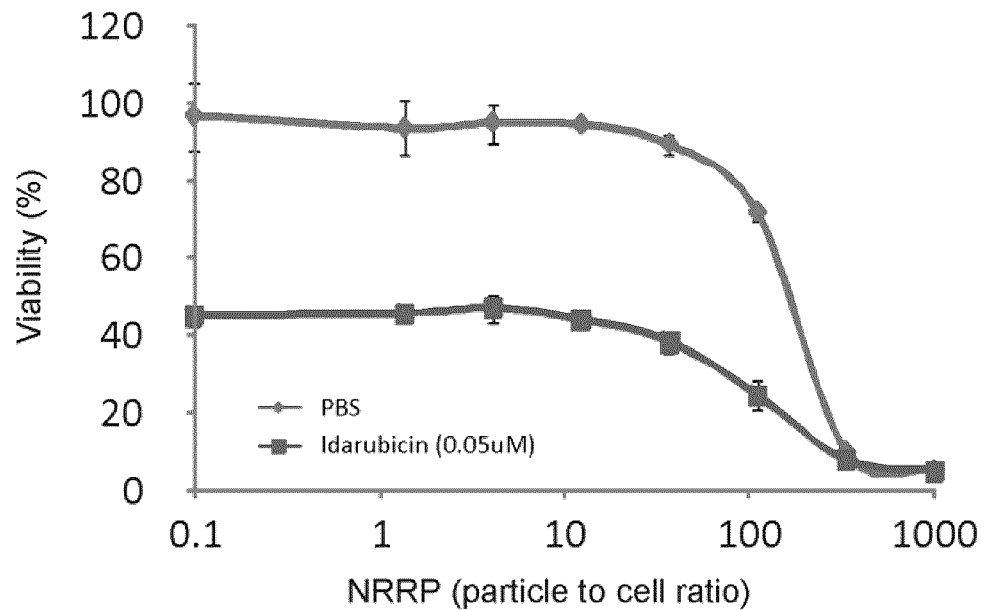
FIG. 14 is a graph illustrating cell viability following a resazurin quantification assay for K562 Ph-positive myeloid leukemic cell line taken 15 hours post treatment with UV-generated NRRPs and the combinatorial effect of UV-generated NRRPs with idarubicin (0.05 μM).

In yet another example, K562 Ph-positive myeloid leukemic cells were treated with UV-generated NRRPs in combination with 0.05 µM irarubicin (FIG. 14) for 72 hours. In this example as well, the myeloid leukemic cell line was highly susceptible to NRRP-mediated cell death and a potentiation-effect was again observed using this class of chemotherapeutic in combination with NRRPs. These observations indicate that NRRP-therapy may indeed be augmented by the use of additional therapeutics. This represents an alternative strategy to treat cancer, particularly recalcitrant forms of cancer that may require this unique combinatorial approach for increased efficacy.

Example 5

Modelling Depicting NRRPs Anti-Tumor Specificity

Figure 15A:
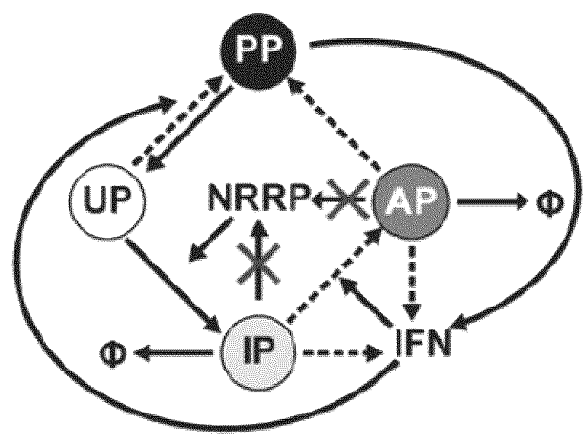
FIG. 15A is an illustration of a phenomenological model developed by Le Boeuf et al. to simulate NRRPs cytotoxicity in normal cells and tumors with defects in antiviral signaling pathways. To describe NRRP kinetics, the original model was modified by removing virus replication (X). Hashed lines describe the IFN-defects associated with tumor cells.

The model used to describe NRRPs specificity against cells with defects in anti-viral signalling pathways was adapted from our previous work described in LeBoeuf et al 2013 (FIG. 15A). Briefly, this model is represented by a subset of six ordinary differential equations describing the transition between the cell populations (UP, IP, AP and PP) depending on the concentration of NRRPs (N) and interferon (IFN) in the environment. These equations are:

$$\frac{dUP}{dt} = -K_{VI} \times [N] \times [UP] - \left(\frac{-K_{IFN\,on}}{1+\left(\frac{[IFN]}{EC50}\right)^2} + K_{IFN\,on}\right) \times [UP] + K_{IFN\,off} \times [PP],$$

$$\frac{dIP}{dt} = K_{VI} \times [N] \times [UP] - \left(\frac{-K_{IFN\,on}}{1+\frac{[IFN]^2}{EC50}} + K_{IFN\,on}\right) \times [IP] - \gamma_c \times [IP],$$

$$\frac{dAP}{dt} = \left(\frac{-K_{IFN\,on}}{1+\frac{[IFN]^2}{EC50}} + K_{IFN\,on}\right)[IP] - K_{VC} \times [AP] - \gamma_c \times [AP],$$

$$\frac{dPP}{dt} = \left(\frac{-K_{IFN\,on}}{1+\frac{[IFN]^2}{EC50}} + K_{IFN\,on}\right)[UP] + K_{VC} \times [AP] - K_{IFN\,off} \times [PP].$$

The parameters used in the above equations represent the NRRP internalization rate ($K_{NI}$), the rate of IFN-signaling activation ($K_{IFN\,on}$), the rate of IFN-signaling inactivation ($K_{IFN\,off}$), the $EC_{50}$ of IFN ($EC_{50}$), the rate of cell death ($\gamma_C$) and the rate NRRP clearance ($K_{NC}$).

The next subset of equation describes the dynamics of NVRPs (N) and interferon (IFN) whereby:

$$\frac{dN}{dt} = -K_{VI} \times [V] \times [UP] - \gamma_V \times [V],$$

$$\frac{dIFN}{dt} = K_{IFN1} \times [IP] + K_{IFN2.1} \times [AP] + K_{IFN2.2} \times [PP] - \gamma_{IFN} \times IFN.$$

The parameters described in the above equations represent the rate of NRRP internalization ($K_{NI}$), NRRP degradation ($\gamma_N$), IFN production from IP, AP and PP ($K_{IFN1}$, $K_{IFN2.1}$ and $K_{IFN2.2}$, respectively) and IFN degradation ($\gamma_{IFN}$).

Figure 15B:
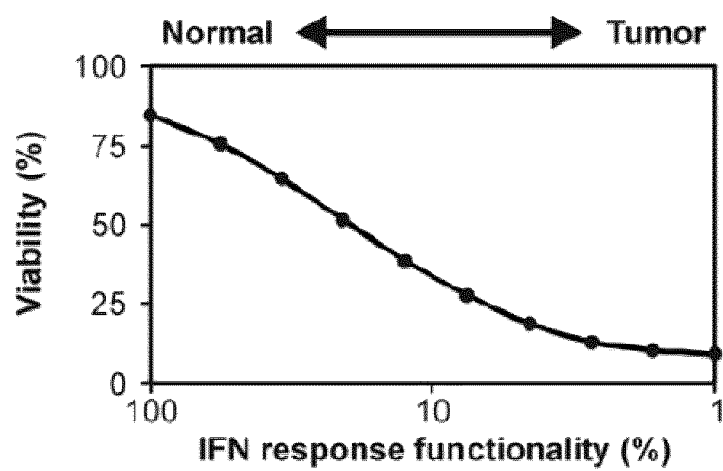
FIG. 15B is a graph showing the simulated relationship between defects in the antiviral signaling pathway and viability post-treatment with NRRPs at 72 hrs.

The Monte Carlo simulation was performed by randomly varying the above parameters within a 1 log window (Table 2) surrounding physiological parameter derived from literature and experimental evidence (18). Simulations were performed in Matlab using ODE15s imposing a none-negativity constraint. Trends described in FIG. 15B represent the median value over 1000 simulations. The number of cells used in these simulations was 2.5E5, the media volume was set at 1 ml, and the PFU to cell ratio was set at 100 particles per cell. In these simulation, defects in IFN-signalling pathways were simulated by decreasing $K_{IFN1}$, $K_{IFN2.1}$, $K_{IFN2.2}$, $K_{VC}$ and $K_{IFN\,on}$ from 100% to 1% of their original value.

To investigate the mechanism by which specificity against the tumor cells is achieved, the authors of the present disclosure simulated the cytotoxicity induced by NRRPs in normal and tumor cells. Recently, the authors of the present disclosure have developed a population-based model describing the relationship between cytotoxicity and live oncolytic virus replication dynamics in normal and tumor cells. According to this model, an infection cycle begins as the uninfected population of cells (UP) encounters virions. This allows the UP population to become infected, and, in the context of live virus, virions and the cytokine known as interferon (IFN) are released into the environment.

As IFN gradually increases, the population of cells activates antiviral signalling (AP) which over time allows this population to clear the viral infection and become protected against further insult (PP). To adapt this model to NRRPs, the authors of the present disclosure removed virus replication dynamics from the model, and simulated the relationship between NRRP-mediated cytotoxicity and the extent of defects in IFN signaling pathways, a process known to occur in ~80% of cancers. These defects were simulated by decreasing the rate of IFN production, the rate of activation of IFN signaling and the rate of NRRP clearance between tumor and normal cells. To ensure that this observation is systematic, a Monte-Carlo simulation platform was utilized. Here, all kinetic parameters were varied within a 1 log window surrounding estimates derived from literature or experimental evidence (Table 2).

Figure 15C:
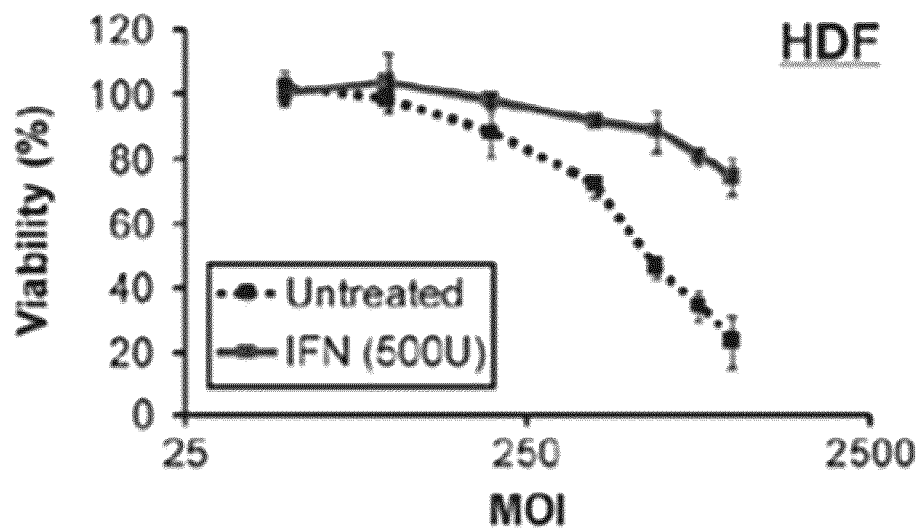
FIG. 15C is a graph showing the in vitro relationship between MOI and viability 72 h post-infection with NRRPs in normal HDF cells in the presence or absence of IFN.
Figure 15D:
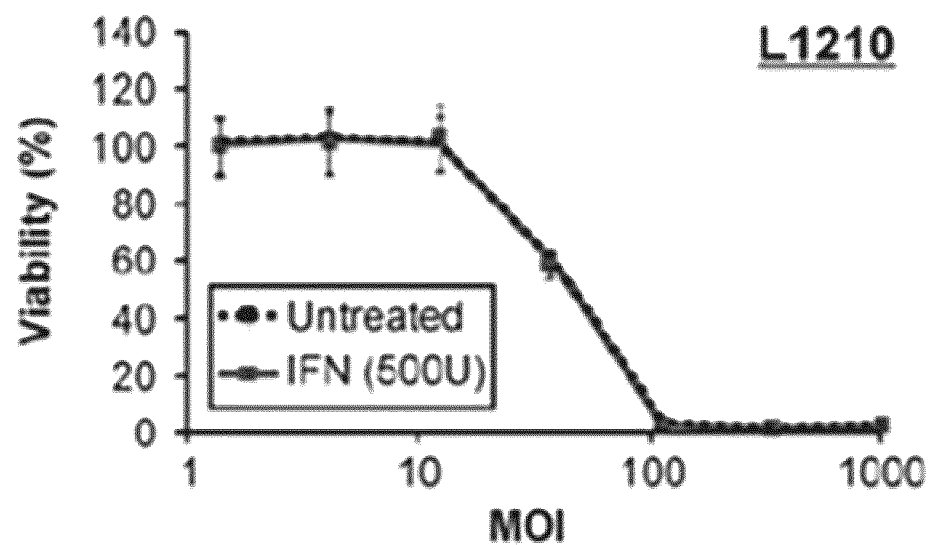
FIG. 15D is a graph showing the in vitro relationship between MOI and viability 72 h post-treatment with NRRPs in leukemic L1210 cells in the presence or absence of IFN.

Following simulation across 1000 random parameter pairings (FIG. 15B), the authors of the present disclosure determined that as the cancer cells lose their ability to signal or respond to IFN, these cells becomes more sensitive to NRRP-mediated cytotoxicity. To validate this observation, the authors of the present disclosure investigated the impact of IFN on NRRP-mediated cytotoxicity in normal (HDF) and leukemic (L1210) cells. Interestingly, while the IntronA (recombinant IFN) could further increase normal cell protection against NRRP insult (FIG. 15C), IntronA had no detectable impact on leukemic cells (FIG. 15D).

Table 2: List of parameters estimates surrounding the experimental and literature evidence described by Le Boeuf et al (2013)

TABLE 2

| Parameter | Range Utilized |
|---|---|
| $K_{NI}$ | 7.5E−5 to 7.5E−4 ($V^{-1}h^{-1}$) |
| EC50 | 0.25e−12 to 2.5e−12 (M) |
| $K_{IFN\,on}$ | $\ln(2)/(0.2$ to $2.0)$ ($h^{-1}$) |
| $K_{IFN\,off}$ | $\ln(2)/(5$ to $50)$ ($h^{-1}$) |
| $\gamma_C$ | $\ln(2)/(2.5$ to $25)$ ($h^{-1}$) |
| $K_{NC}$ | $\ln(2)/(0.25$ to $2.5)$ ($h^{-1}$) |
| $K_{IFN1}$ | $K_{IFN2} \times 10$ to 100% (M/h) |
| $K_{IFN2.1}$ & $K_{IFN2.2}$ | 8.3e−18 to 8.3e−17 (M/cell/h) (ie 5000-50000 molecules/cell/h) |
| $\gamma_{IFN}$ | $\ln(2)/(5$ to $50)$ ($h^{-1}$) |
| $\gamma_N$ | $\ln(2)/(2.5$ to $25)$ ($h^{-1}$) |

Example 6

NRRP Activity in AML Blast Crisis

Figure 16A:
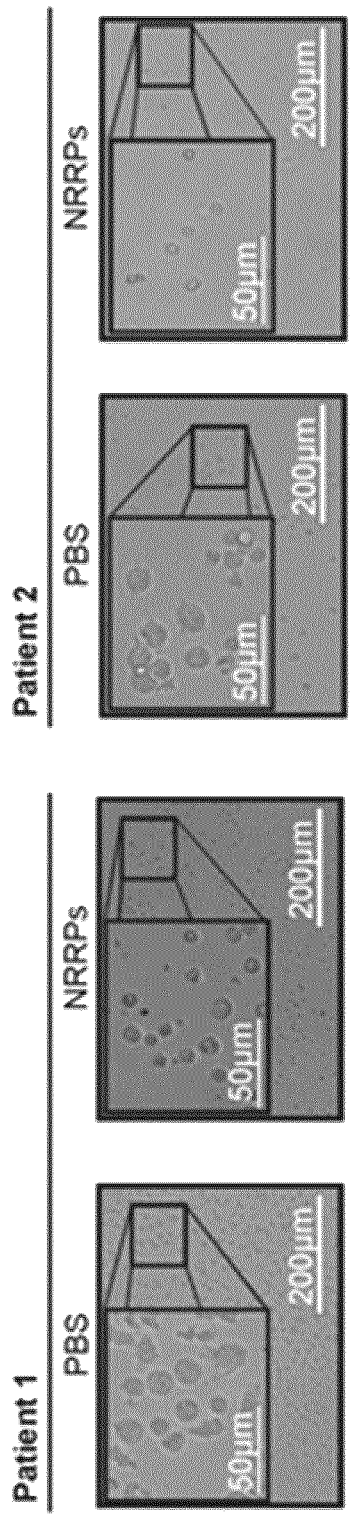
FIG. 16A is a set of brightfield microscopy images of two Chronic Myeloid Leukemia-blast crisis patient samples treated with PBS or NRRPs.
Figure 16B:
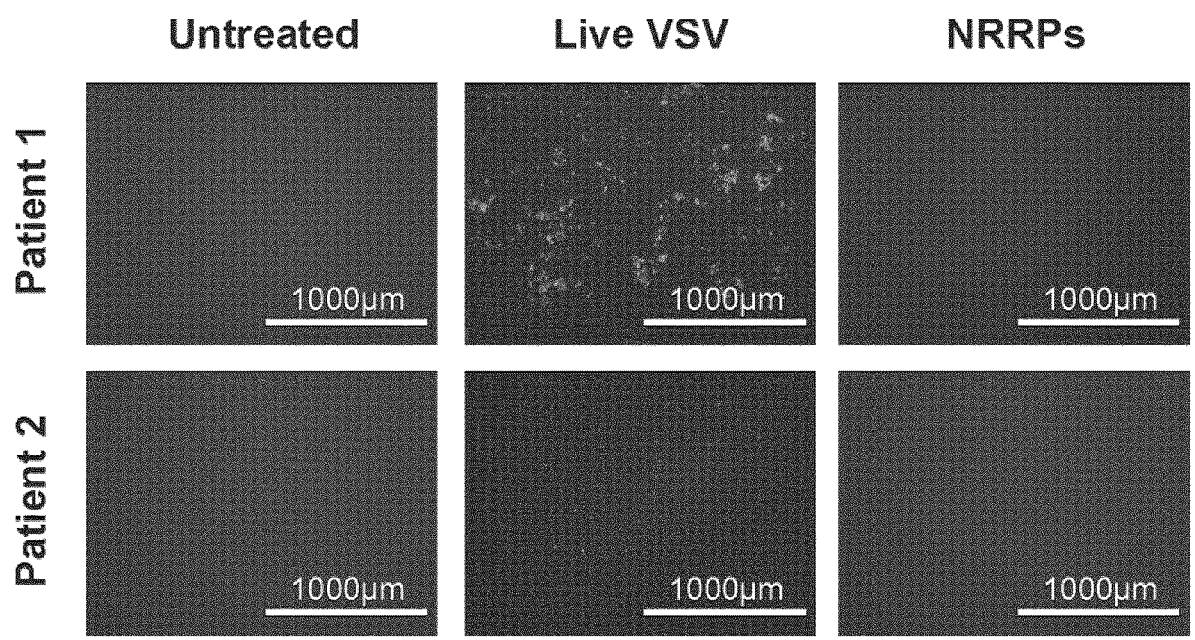
FIG. 16B is a set of fluorescent microscopy images (4×) of acute leukemia (CML blast-crisis) from human patient peripheral blood samples. Leukemia enriched samples collected from peripheral blood treated with PBS, Live VSV-GFP, or NRRPs encoded for GFP. Images are 24 h post infection at MOI=100.
Figure 16C:
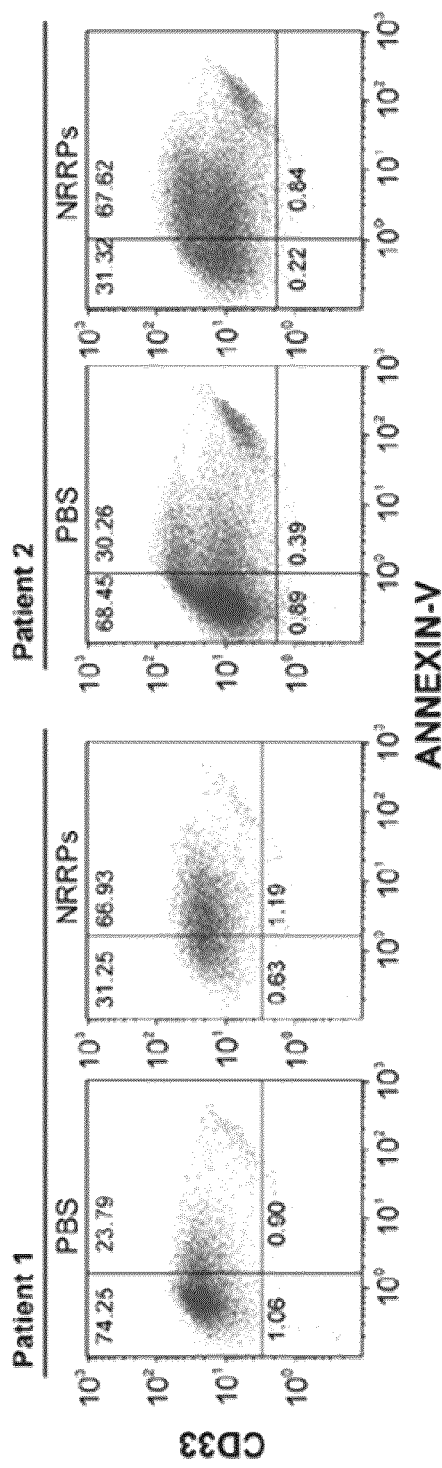
FIG. 16C is a flow cytometry diagram complementing the data presented in FIGS. 16A and 16C of Annexin-V and CD33 staining in two CML-blast crisis patient samples treated with PBS or NRRPs (MOI=100) 48 h post-treatment. The CD33+ blast population was enriched by long term culture of the cells.
Figure 16D:
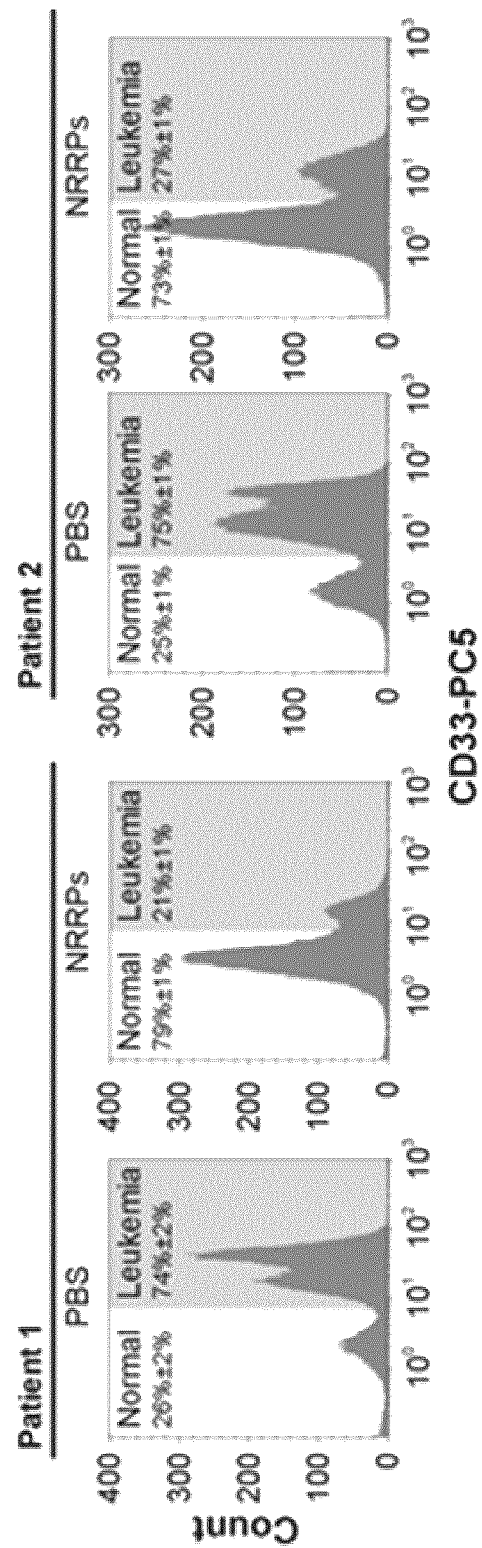
FIG. 16D are graphs showing flow cytometry analysis of CD33 staining in the two CML-blast crisis patient samples treated with PBS or NRRPs.

The translational potential of the NRRP platform was investigated in clinical samples. Peripheral blood mononuclear cells were obtained from two human patients with high-burden acute blast crisis, and susceptibility towards NRRP-mediated cell death was tested. The patients had circulating blasts with a CD33 positive phenotype. Both had previously received extensive treatment for chronic myeloid leukemia (CML) and developed resistance to tyrosine kinase inhibitor (TKI) treatment. Similar to the observation in L1210 blast cells, patient samples developed obvious NRRP-induced apoptosis with the classic morphology (FIG. 16A). Fluorescence microscopy confirmed the absence of NRRP genome expression (FIG. 16B). Indeed post NRRP-treatment these CD33+ leukemia cells stained strongly for the apoptotic marker Annexin V (FIG. 16C). Use of the non-cultured patient samples was used to evaluate specificity of this response. Indeed in both patients, the preponderant leukemic CD33+ population was ablated following NRRP treatment, leaving normal cells to dominate the sample (FIG. 16D).

Figure 17A:
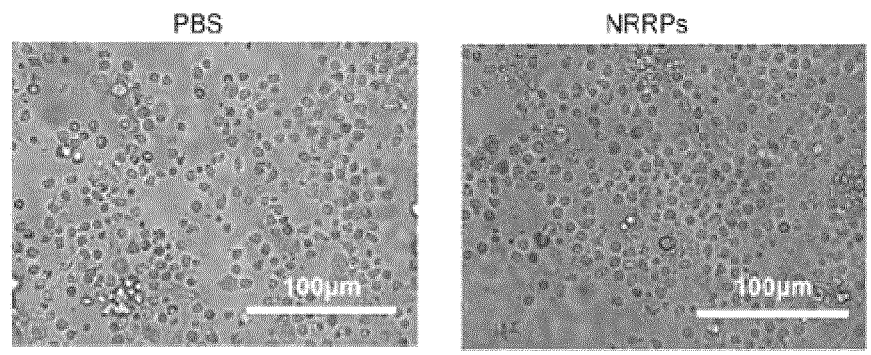
FIG. 17A is a set of brightfield microscopy images of a healthy bone marrow sample treated with PBS or NRRPs for 18 hours.
Figure 17B:
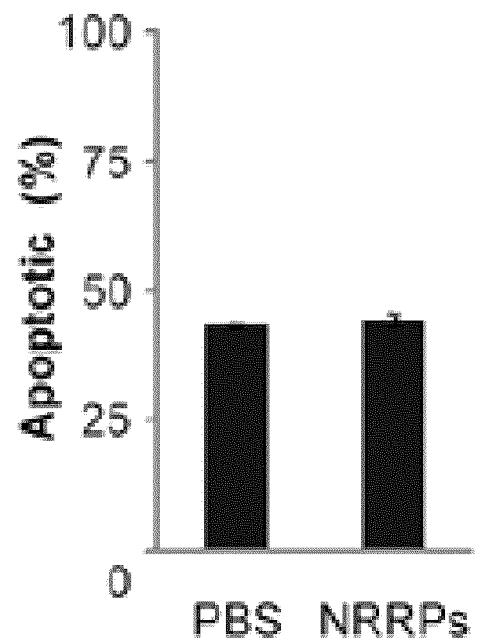
FIG. 17B is a graph showing the quantification of Annexin-V staining in the healthy bone marrow sample treated with PBS or NRRPs for 65 hours.

To ensure that NRRPs do not affect normal white blood cells, bone marrow mononuclear cells isolated from a healthy donor were treated with PBS or NRRPs. At both early (18 hour) and late (65 hour) time points, NRRPs did not induce apoptosis within these samples (FIGS. 17A and 17B).

Example 7

NRRP Anti-Leukemic Activity In-Vivo

Figure 18A:
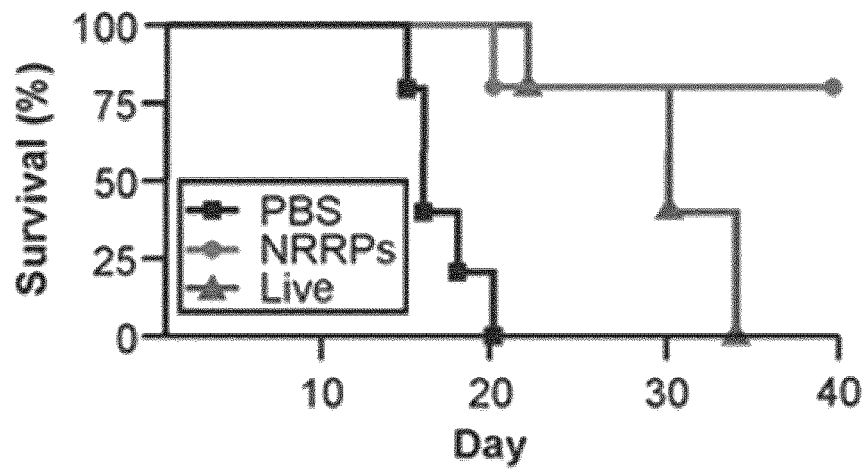
FIG. 18A is a graph showing the survival curve in a murine blast crisis treatment model. Following L1210 challenge in mice on day 1, mice received three daily doses NRRPs or PBS.

A murine model of leukemic blast crisis was used to evaluate the potential of NRRPs as a therapeutic agent. Briefly, on day one, DBA/2 mice were challenged with $1 \times 10^6$ dose of L1210 blast cells. The following day, mice began a regimen of $3 \times 10^9$ NRRPs administered intravenously for three consecutive days, and survival was monitored. In parallel, separate cohorts of mice were treated with live VSV at the MTD of $2 \times 10^6$ virus per injection (19), or PBS under the same treatment schedule. NRRP treated mice achieved 80% survival up to day 40, representing a significant advantage versus those treated with PBS (P≤0.0045) or live virus (P≤0.044) (FIG. 18A). NRRPs were well tolerated and administered at the maximal feasible dose for this particular experiment, which represented a 1500× higher dose than the MTD of live virus. Given that acute leukemia frequently disseminates to the central nervous system, and that wild type VSV is highly neurotoxic, intracranial injections of NRRPs and live virus were performed. While mice could tolerate the maximum production dose for intracranial injections of $1\times10^8$ particles, all mice rapidly succumbed to a $1\times10^4$ dose of live virus.

Figure 18B:
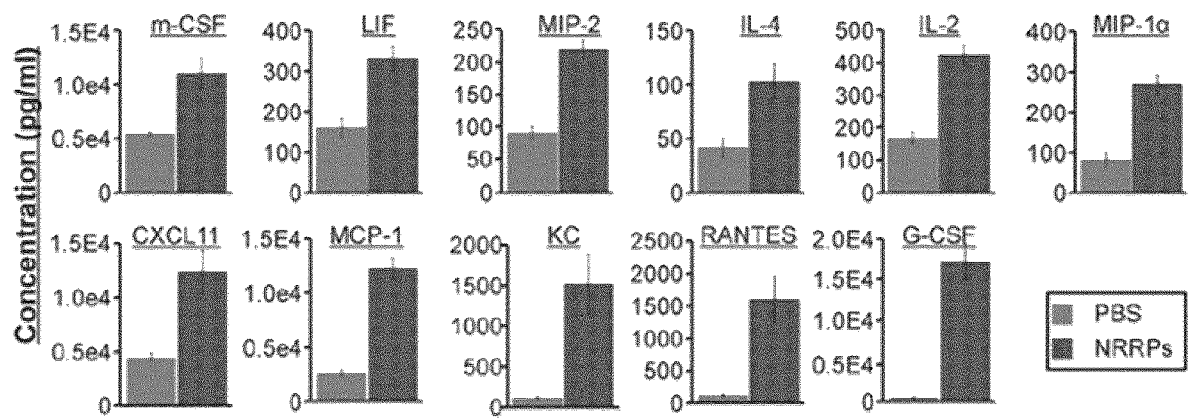
FIG. 18B is a set of graphs showing Luminex-based quantification of cytokines induced by NRRPs in L1210 bearing mice during acute blast crisis. All identified cytokines are induced over 2 fold by NRRP-treated mice and are statistically significant (non-paired t-test pV<0.05). pV has been corrected to account for multiple hypothesis testing (Benjamini & Hochberg Method).

Prompted by the efficacy and differential MTD afforded by NRRP therapy, it is interesting to know whether the immune system is activated following treatment. Murine blood serum was collected from L1210 tumor bearing mice 20 hours after PBS or NRRPs treatment (FIG. 18B). In this analysis, it is clear that cytokines typically known to recruit and differentiate T-cells are induced following NRRP treatment. Examples of such immune-modulatory cytokines significantly induced by NRRP treatment include the leukemia inhibitory factor LIF, IL-2, IL-4, CCL-2, RANTES and MIP-1α (FIG. 18B).

To confirm immune system stimulation, in particular T-cell activation, the authors of the present disclosure adopted a vaccine strategy described in previous publications. Experimentally, this platform consists of injecting apoptotic cells into immunocompetent animals and measuring protective adaptive immunity against subsequent tumor challenge. Indeed, L1210 cells treated with NRRPs develop marked apoptosis as can be seen in FIG. 16C by the increase in Annexin-V staining. Therefore, this classical experimental approach was adopted to explore whether NRRPs trigger immunogenic apoptosis.

Figure 19:
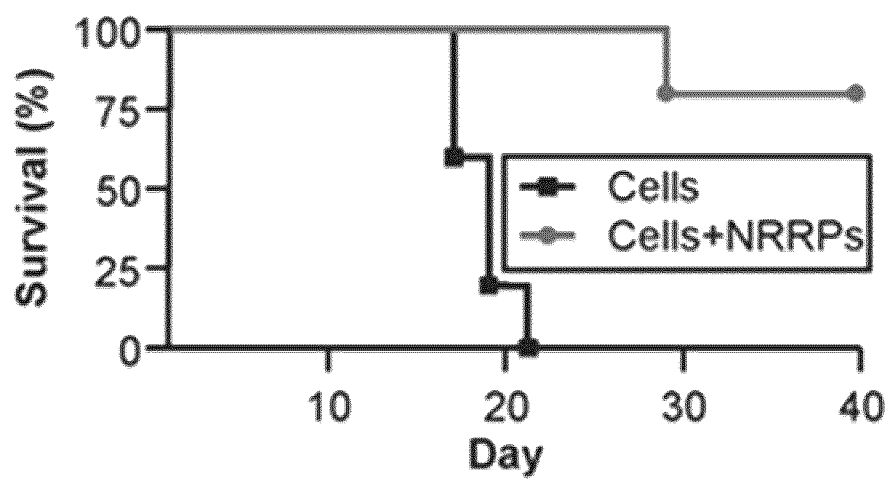
FIG. 19 is a graph showing the survival curve in a murine immunocompetent model of immunogenic apoptosis. Prior to L1210 challenge on day 1, mice received three weekly doses of γ-irradiated L1210 cells incubated or not incubated with NRRPs.

Two cohorts of DBA/2 mice (syngeneic to L1210) received three weekly intravenous doses of $1\times10^6$ γ-irradiated L1210 cells pre-treated with NRRPs. Another cohort received the same number of γ-irradiated L1210 cells. One week following this regimen, a L1210 leukemic challenge ($1\times10^6$ cells) was administered via tail vein, and survival recorded. The cohort receiving NRRP-treated L1210 cells had 80% protection after leukemic challenge, which was otherwise uniformly lethal in the untreated L1210-administered cohorts (FIG. 19). Surviving mice were kept for >150 days to ensure long-lasting protection. This is consistent with the notion that NRRP-treated acute leukemia cells undergo immunogenic apoptosis.

Using acute lymphoblastic and myeloid leukemia cell lines, as well as primary leukemia cells from heavily pre-treated CML patients in acute blast crisis, it is demonstrated that NRRPs are at least leukemia-specific cytolytic agents. Through the in-vitro and in-vivo experiments detailed above, it is confirmed that NRRPs offer a multimodal therapeutic platform.

Example 8

NRRP Activity in Multiple Myeloma, Brain Cancer and Colon Cancer Cell Lines

Figure 20:
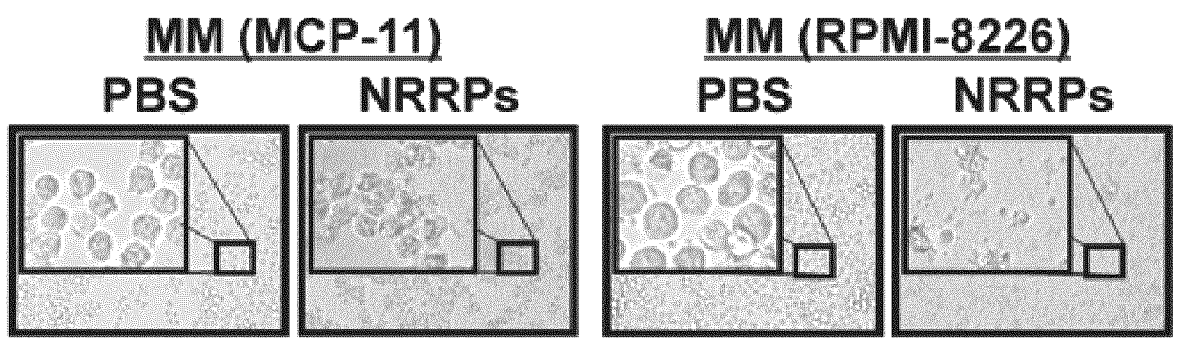
FIG. 20 is a set of brightfield microscopy images of myeloma cell lines MPC-11 and RPMI-8226 taken 15 hours post treatment with PBS or NRRPs. NRRPs were administered at an MOI=250, a dose previously determined to have no impact on normal cell viability.
Figure 21:
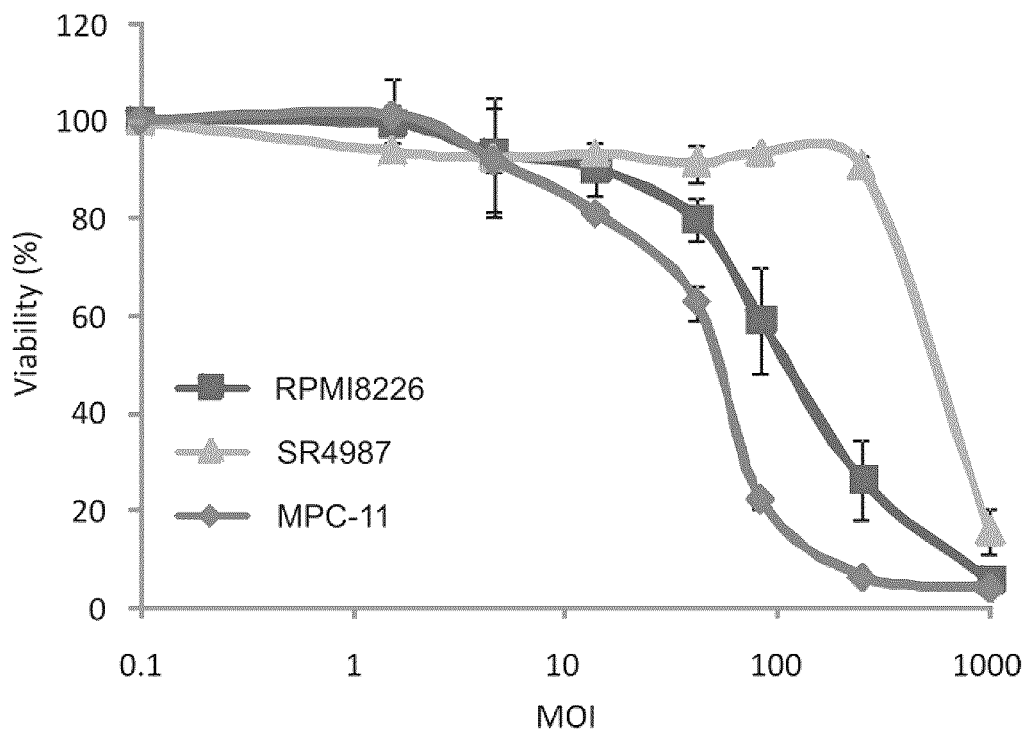
FIG. 21 is a graph showing cell viability following an resazurin quantification assay for myeloma cell lines MPC-11 and RPMI-8226 taken 15 hours post treatment with NRRPs administered at an MOI=250. SR4987 is a normal marrow stromal cell line.

In addition to the experiments detailed above, NRRPs were also shown to be cytopathic in multiple myeloma cell lines MCP-11 and RPMI-8226 (FIG. 20) when the cells lines were treated with PBS or VSV-derived NRRPs for 15 hours. Specifically, FIG. 21 shows cell viability following an Alamar blue cytotoxicity or resazurin assay for myeloma cell lines taken 72 hours post treatment with NRRPs administered at an MOI=250. In this experiment, SR4987 is a normal marrow stromal cell line. As seen in FIG. 21, SR4987 demonstrates resistance to NRRPs as it is a non-malignant cell. No NRRP or VSV genome replication was found when the NRRPs were generated, since no viral-encoded GFP was produced (data not shown).

Figure 22:
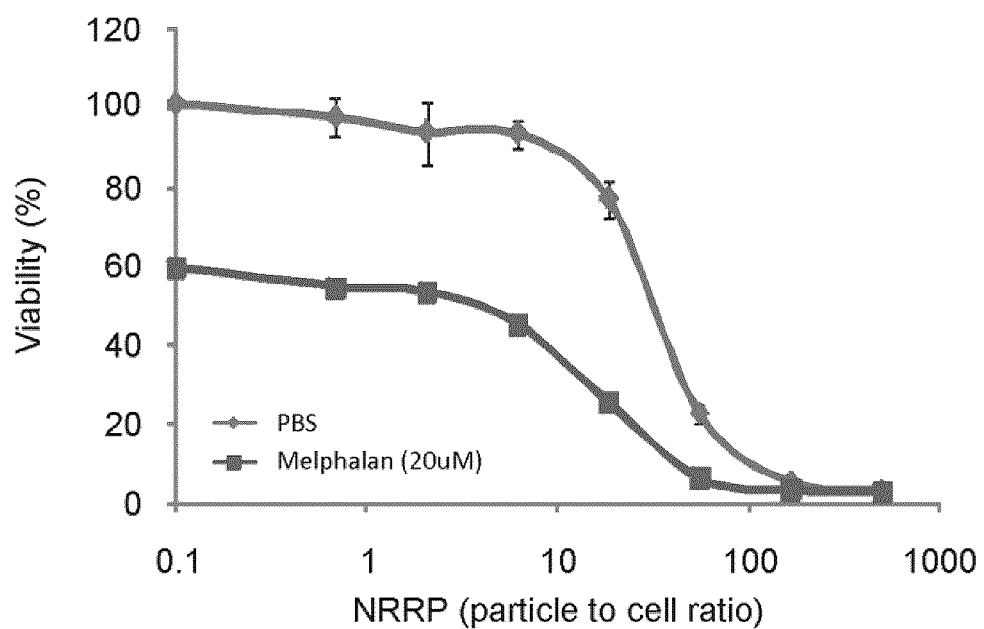
FIG. 22 is a graph illustrating cell viability following a resazurin quantification assay for MPC-11 multiple myeloma cell line taken 72 hours post treatment with UV-generated NRRPs and the combinatorial effect of UV-generated NRRPs with melphalan (20 μM).
Figure 23:
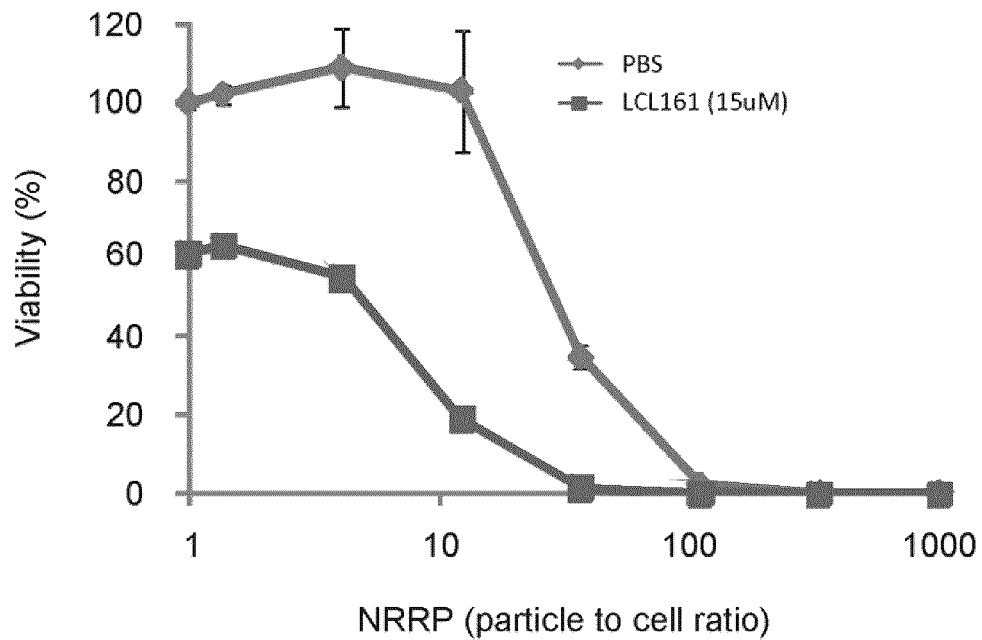
FIG. 23 is a graph illustrating cell viability following a resazurin quantification assay for MPC-11 multiple myeloma cell line taken 72 hours post treatment with UV-generated NRRPs and the combinatorial effect of UV-generated NRRPs with the second mitochondria-derived activator of caspase (SMAC) mimetic, LCL161(15 μM).

In another example, MCP-11 multiple myeloma cell line was treated with 20 melphalan (FIG. 22) or 15 μM SMAC mimetic LCL161 (FIG. 23) in combination with NRRPs. Combination therapy augmented the cytopathic effect of NRRPs in both cases. Synergistic activity between SMAC mimetics and NRRPs represents a promising approach. It is observed that SMAC mimetic anti-tumor activity is significantly augmented or in some cases essentially dependent-upon NRRP co-administration.

Figure 24:
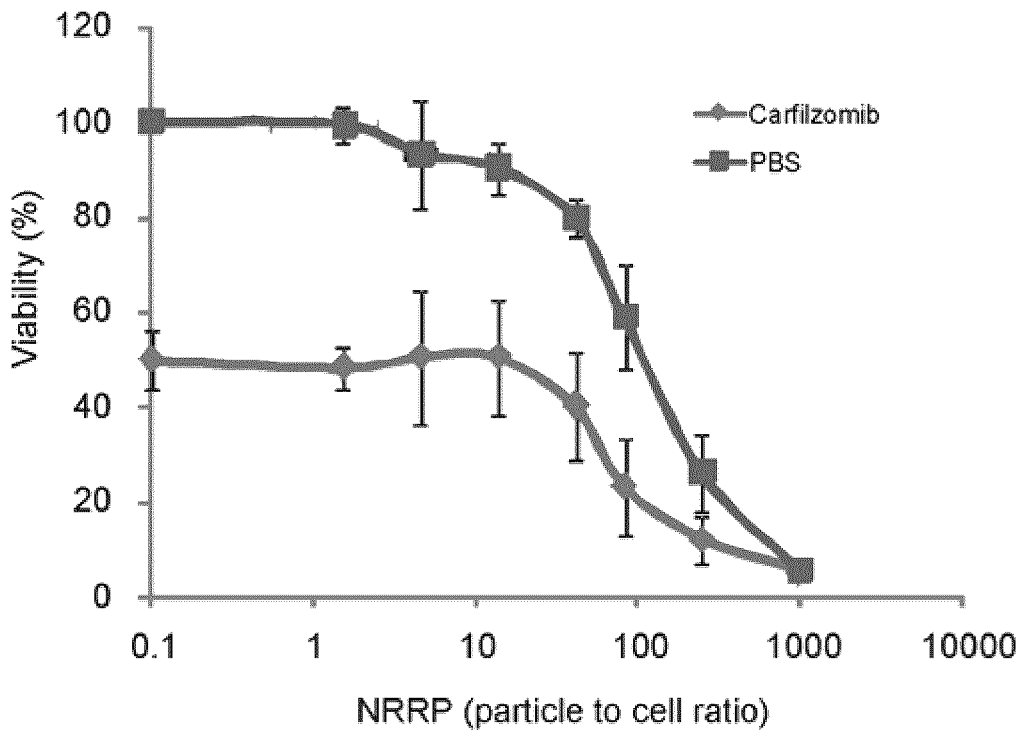
FIG. 24 is a graph illustrating cell viability following a resazurin quantification assay for RPMI-8226 multiple myeloma cell line taken 72 hours post treatment with UV-generated NRRPs and the combinatorial effect of UV-generated NRRPs with carfilzomib (5 nM).

In yet another example, RPMI-8226 multiple myeloma cell line was treated with 5 nM carfilzomib with potentiating cytotoxic effect (FIG. 24). It is demonstrated that co-administration of NRRPs with an alkylating agent (such as melphalan), a proteasome inhibitor (such as carfilzomib) or a SMAC mimetic (such as LCL161) represents an alternative treatment strategy for various cancers, particularly promising in hematopoietic-based cancers, such as multiple myeloma.

Figure 25A:
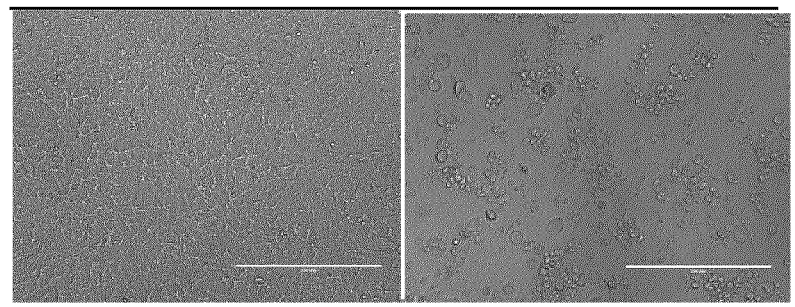
FIG. 25A is a set of brightfield microscopy images of a mouse delayed brain tumor glioblastoma cell line (DBT) taken 24 hrs post treatment with PBS or NRRPs.
Figure 25B:
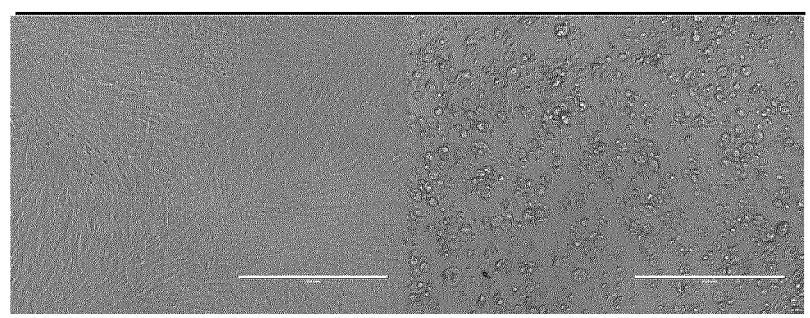
FIG. 25B is a set of brightfield microscopy images of an astrocytoma cell line (K1491) taken 24 hrs post treatment with PBS or NRRPs.
Figure 25C:
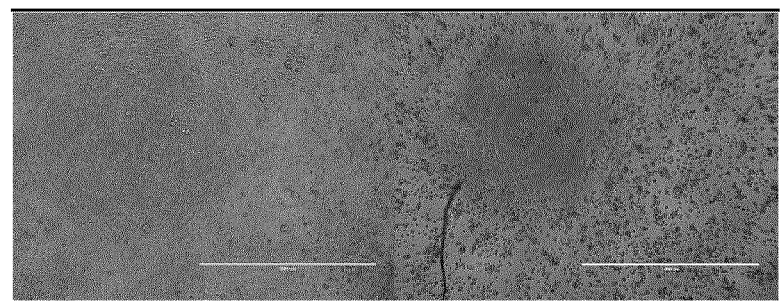
FIG. 25C is a set of brightfield microscopy images of a mouse glioma cell line (GL261) taken 24 hrs post treatment with PBS or NRRPs.
Figure 26:
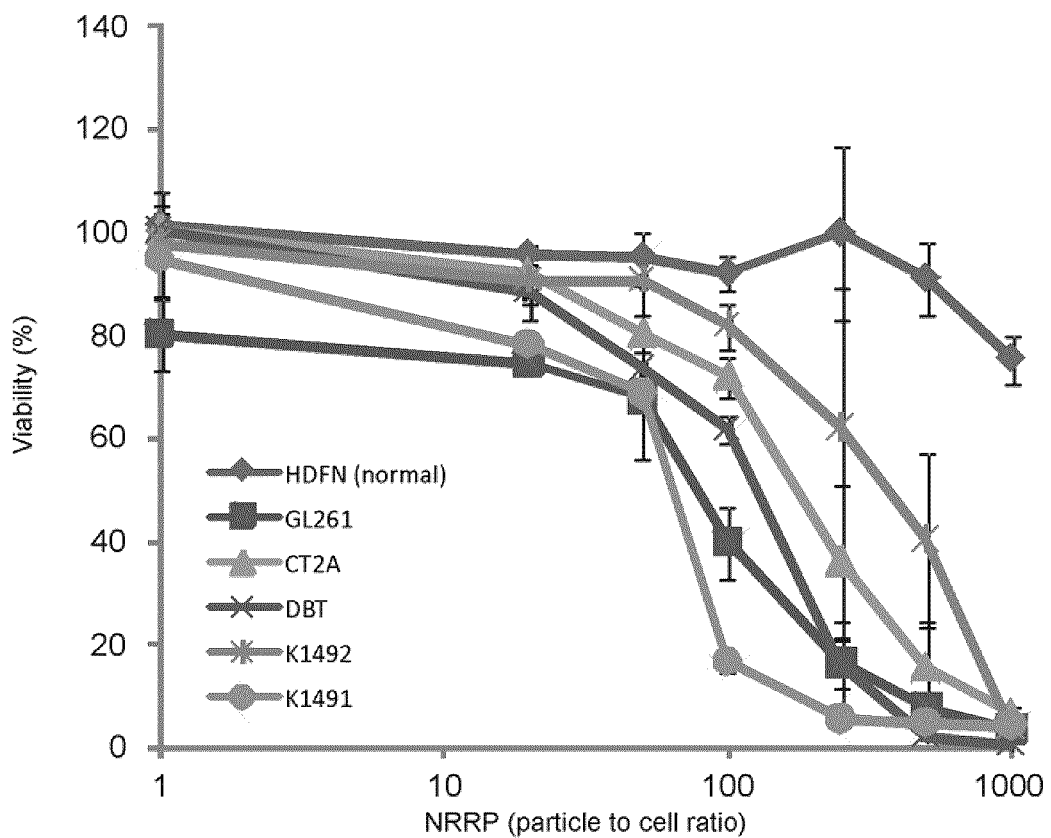
FIG. 26 is a graph showing cell viability following a resazurin quantification assay for brain cancer cell lines DBT, K1491, K1492, CT2A, and GL261 relative to normal HDFN control.

The usefulness of NRRPs as an anti-cancer therapeutic is further demonstrated by its effect on brain tumor cell lines. NRRPs-mediated cytotoxicity was determined in glioblastoma cell line CT2A, delayed brain tumor glioblastoma cell line (DBT) (FIG. 25A), astrocytoma cell lines K1491 (FIG. 25B) and K1492, and mouse glioma cell line (GL261) (FIG. 25C), compared to HDNF normal cells, when these cells were treated for 24 hrs with PBS or NRRPs (FIG. 26).

Figure 27:
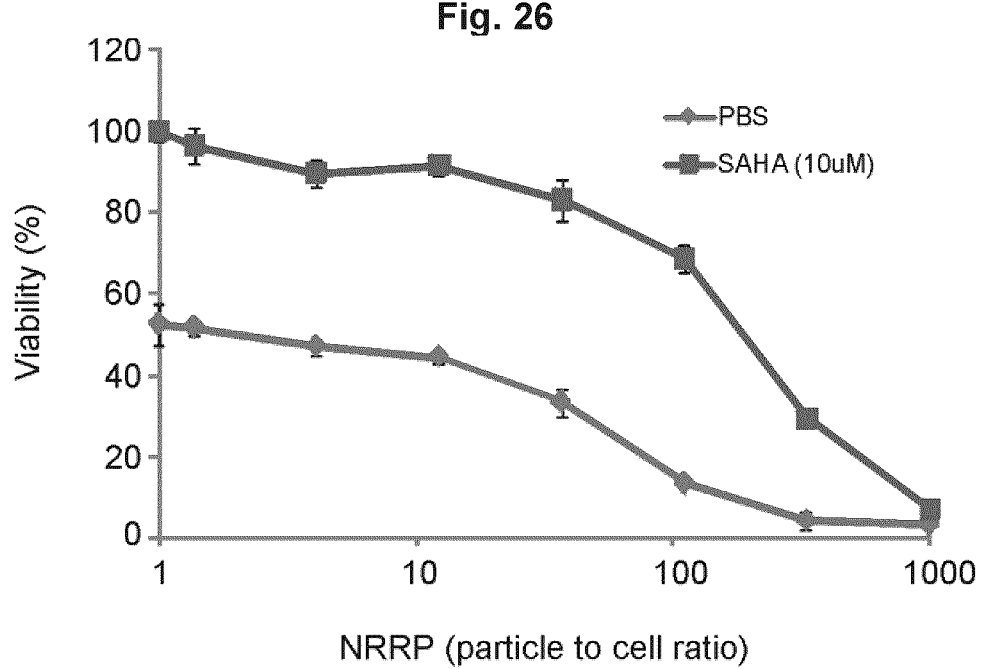
FIG. 27 is a graph illustrating cell viability following a resazurin quantification assay for CT2A glioblastoma cell line taken 72 hours post treatment with UV-generated NRRPs and the combinatorial effect of UV-generated NRRPs with the HDAC inhibitor SAHA (10 μM).

Also, in yet another example, glioblastoma cell line CT2A was treated with 10 μM of the HDAC inhibitor SAHA in combination with NRRPs and a potentiation cytopathic effect was observed compared to NRRPs with PBS (FIG. 27). HDAC inhibition has shown a modicum of promise as an anti-cancer agent. However, in combination with NRRPs, significant activity is noted, representing a very promising approach to treat glioblastoma-based malignancies, an unmet clinical need.

Figure 28A:
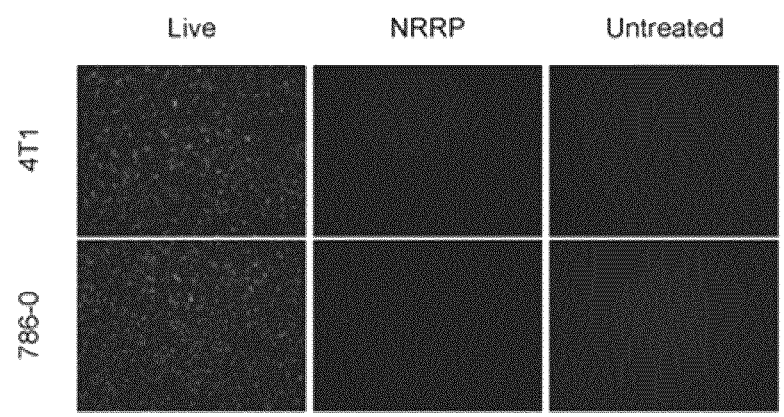
FIG. 28A is a set of fluorescent microscopy images (4×) of NRRP-mediated tumor cell cytotoxicity in resistant solid tumor cell lines. The set of images show mouse mammary or breast (4T1) and human kidney (786-0) cancer cells treated with PBS, Live VSV, and NRRPs. Images were taken at 24 h post infection.
Figure 28B:
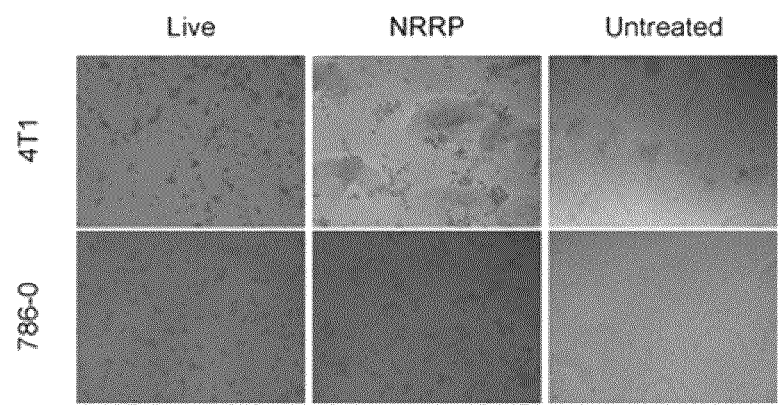
FIG. 28B is a set of brightfield microscopy images taken at 72 h post infection of NRRP-mediated tumor cell cytotoxicity in resistant solid tumor cell lines, in breast (4T1) and kidney (786-0) cancer cells treated with PBS, Live VSV, and NRRPs.
Figure 28C:
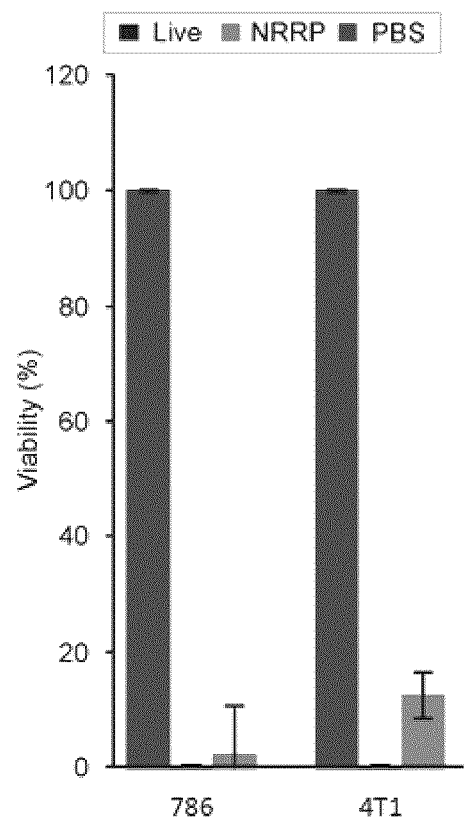
FIG. 28C is a graph showing resazurin quantification of cellular viability in resistant solid tumor cell lines, in breast (4T1) and kidney (786-0) cancer cells treated with PBS, Live VSV, and NRRPs, 72 h post infection.

Renal (786-0) and breast cancer (4T1) cell lines are equally sensitive to the cytopathic effects of NRRPs (FIGS. 28A, 28B, 28C). In this series of experiments, cell lines were treated with NRRPs at an MOI=250 and viability was quantified by resazurin assay over a 72 h period. Fluorescence microscopy performed throughout the experiment confirmed the absence of genome expression.

Figure 29:
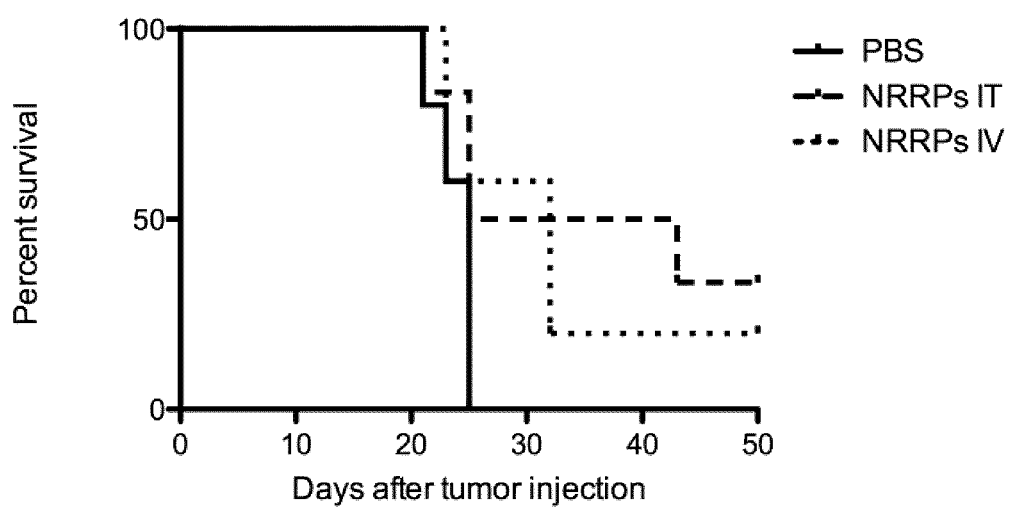
FIG. 29 is a graph illustrating survival advantage in sub-cutaneous CT-26 colon cancer treated with 2E9 UV-generated NRRPs on days 16, 18 and 21 post tumor embedment.

In another example, subcutaneous CT26 colon cancer cells were implanted into mice. The mice were then treated with 2E9 NRRPs on days 16, 18 and 21 post tumor embedment (FIG. 29). Despite large tumor burden prior to NRRP-treatment, prolonged survival and cures were obtained when NRRPs were administered via the intratumoral or intravenous routes. PBS control-treated mice all rapidly reached endpoint. This model represents additional evidence that solid tumors may also be amenable to NRRP-based regimens.

The Examples above show through in-silico and in-vitro testing that NRRPs, analogous to live virus, are tumor-selective given that they exploit defects in innate immune pathways common to most tumors. However, the safety margin afforded by the NRRP platform was exemplified by the observation that high titer intracranial NRRP administration was well tolerated by murine recipients.

The outcome for the majority of adult patients suffering from acute lymphoblastic or acute myeloid leukemia remains dismal. For a minority of patients, allogeneic stem cell transplantation after myeloablative conditioning is potentially curative, however this procedure is associated with frequent adverse events and significant treatment-related mortality. For many patients with chronic-phase CML, targeted tyrosine kinase inhibitor therapy offers excellent disease control. When progression into acute blast crisis occurs, very limited therapeutic options exist due to development of multi drug resistance and the rapid kinetics of this form of recalcitrant leukemia.

NRRPs exhibit both direct cytolytic and immunogenic properties in multiple acute leukemia murine models. A peculiar form of programmed cell death involves the induction of adaptive immune responses against the dying cell. This process, commonly referred to as immunogenic apoptosis, is essential to the efficacy of several current chemotherapeutics and is required for host defense against viral infection including live RVs. The in-vivo results above indicate that a similar process is induced by NRRPs and is a driving factor to treatment efficacy.

More relevant are the observations that multi-drug resistant primary myeloblasts from patients in CML blast-crisis are forced into apoptosis and finally eradicated by NRRP treatment. In addition, non-leukemic white cells procured from healthy bone marrow were not adversely affected. This observation suggests that despite the potent tumoricidal activity of NRRPs, the leukopenia commonly observed after standard induction and consolidation chemotherapy could be avoided. This may significantly decrease treatment related adverse events. Further, given the preservation of normal white blood cells during leukemic cytoreduction by NRRPs, the simultaneous induction of an effective anti-leukemic immune response may be attainable for the majority of patients who are not candidates for high-dose radio-chemotherapy followed by allogeneic stem cell transplantation. Following the induction of immunogenic apoptosis by NRRPs, a broad array of immunomodulatory cytokine are released and likely assist in the development of effective adaptive immune activity—a critical component to achieving durable curative responses.

The Examples demonstrate the production of high-titer NRRPs. Through the induction cell lysis mainly via programmed cell death pathways, systemic and intratumoral immune responses, including natural killer cell activation as well as dendritic cell activation, or vasculature shutdown within the tumor—NRRPs harbor several anti-cancer properties. These features may be exploited by using NRRPs alone or as an adjuvant in combination with radiation therapies, chemotherapies, immuno-therapies, surgery, oncolytic-virus derived or other virus-derived therapeutic platforms.

In the preceding description, for purposes of explanation, numerous details are set forth in order to provide a thorough understanding of the examples. However, it will be apparent to one skilled in the art that these specific details are not required.

The above-described examples are intended to be exemplary only. Alterations, modifications and variations can be effected to the particular examples by those of skill in the art without departing from the scope, which is defined solely by the claims appended hereto.

REFERENCES

1. Hanahan D, Weinberg R A. The hallmarks of cancer. Cell 2000; 100: 57-70.
2. Hanahan D, Weinberg R A. Hallmarks of cancer: The next generation. Cell 2011; 144: 646-674.
3. Liu B L, Robinson M, Han Z-, Branston R H, English C, Reay P, et al. ICP34.5 deleted herpes simplex virus with enhanced oncolytic, immune stimulating, and anti-tumour properties. Gene Ther 2003; 10: 292-303.
4. Senzer N, Bedell C, Nemunaitis J. OncoVEXGM-CSF. Armed oncolytic virus. Drugs of the Future 2010; 35: 449-455.
5. Park B-, Hwang T, Liu T-, Sze D Y, Kim J-, Kwon H-, et al. Use of a targeted oncolytic poxvirus, JX-594, in patients with refractory primary or metastatic liver cancer: a phase I trial. The Lancet Oncology 2008; 9: 533-542.
6. Breitbach C J, Thorne S H, Bell J C, Kirn D H. Targeted and armed oncolytic poxviruses for cancer: The lead example of JX-594. Curr Pharm Biotechnol 2012; 13: 1768-1772.
7. Breitbach C J, Burke J, Jonker D, Stephenson J, Haas A R, Chow L Q M, et al. Intravenous delivery of a multi-mechanistic cancer-targeted oncolytic poxvirus in humans. Nature 2011; 477: 99-104.
8. Barber G N. VSV-tumor selective replication and protein translation. Oncogene 2005; 24: 7710-7719.
9. Stojdl D F, Lichty B D, TenOever B R, Paterson J M, Power A T, Knowles S, et al. VSV strains with defects in their ability to shutdown innate immunity are potent systemic anti-cancer agents. Cancer Cell 2003; 4: 263-275.
10. Mahoney D J, Lefebvre C, Allan K, Brun J, Sanaei C, Baird S, et al. Virus-Tumor Interactome Screen Reveals ER Stress Response Can Reprogram Resistant Cancers for Oncolytic Virus-Triggered Caspase-2 Cell Death. Cancer Cell 2011; 20: 443-456.
11. Saloura V, Wang L-S, Fridlender Z G, Sun J, Cheng G, Kapoor V, et al. Evaluation of an attenuated vesicular stomatitis virus vector expressing interferon-β for use in malignant pleural mesothelioma: Heterogeneity in interferon responsiveness defines potential efficacy. Hum Gene Ther 2010; 21: 51-64.
12. Brun J, McManus D, Lefebvre C, Hu K, Falls T, Atkins H, et al. Identification of genetically modified maraba virus as an oncolytic rhabdovirus. Molecular Therapy 2010; 18: 1440-1449.
13. Willmon C L, Saloura V, Fridlender Z G, Wongthida P, Diaz R M, Thompson J, et al. Expression of IFN-β enhances both efficacy and safety of oncolytic vesicular stomatitis virus for therapy of mesothelioma. Cancer Res 2009; 69: 7713-7720.
14. Galivo F, Diaz R M, Wongthida P, Thompson J, Kottke T, Barber G, et al. Single-cycle viral gene expression, rather than progressive replication and oncolysis, is required for VSV therapy of B16 melanoma. Gene Ther 2010; 17: 158-170.
15. Swarna Bais, Eric Bartee, Masmudur M. Rahman, Grant McFadden, Christopher R. Cogle. Oncolytic Virotherapy for Hematological Malignancies. Advances in Virology 2012; 8.
16. Zitvogel L, Kepp 0, Senovilla L, Menger L, Chaput N, Kroemer G. Immunogenic tumor cell death for optimal anticancer therapy: The calreticulin exposure pathway. Clinical Cancer Research 2010; 16: 3100-3104.
17. Ebert O, Harbaran S, Shinozaki K, Woo S L C. Systemic therapy of experimental breast cancer metastases by mutant vesicular stomatitis virus in immune-competent mice. Cancer Gene Ther 2005; 12: 350-358.
18. Finke J, Nagler A. Viewpoint: What is the role of allogeneic haematopoietic cell transplantation in the era of reduced-intensity conditioning—Is there still an upper age limit? A focus on myeloid neoplasia. Leukemia 2007; 21: 1357-1362.
19. Daenen S, Van Der Holt B, Dekker A W, Willemze R, Rijneveld A W, Biemond B J, et al. Intensive chemotherapy to improve outcome in patients with acute lymphoblastic leukemia over the age of 40: A phase II study for efficacy and feasibility by HOVON. Leukemia 2012; 26: 1726-1729.
20. Giles F J, O'Dwyer M, Swords R. Class effects of tyrosine kinase inhibitors in the treatment of chronic myeloid leukemia. Leukemia 2009; 23: 1698-1707.
21. Hehlmann R. How I treat CML blast crisis. Blood 2012; 120: 737-747.

What is claimed is:

1. A composition comprising a non-replicating, cell-internalizing Rhabdovirus-derived particle, wherein said Rhabdovirus-derived particle exhibits RNA which is cross-linked or cleaved into at least two discontinuous RNA polynucleotide sequences, and wherein the composition is produced from a 50 µl sample of $1\times10^{10}$ plaque forming units per ml (PFU/ml) live Rhabdovirus subjected to a UV dose of 250 mJ/cm$^2$ for about 40 seconds, the composition inducing less than 40% viability of immortalized cells and about 80% viability of normal non-cancer cells in an in-vitro cytotoxicity assay using a multiplicity of infection of 100 particles per cell.

2. The composition of claim 1, wherein said Rhabdovirus-derived particle exhibits:
RNA cross-linked to other RNA nucleotides, to amino acids in a protein structure around the RNA of the Rhabdovirus, or;
the protein structure around the RNA is cross-linked to another protein of the protein structure, or to another amino acid of the same protein;
or both.

3. The composition of claim 1, wherein said RNA comprises at least 0.05% cross-linked nucleotides.

4. The composition of claim 1, wherein said non-replicating, cell-internalizing Rhabdovirus-derived particle exhibits at least 60 G proteins per particle.

5. The composition of claim 1, wherein the immortalized cells are cancer cells and the normal non-cancer cells are human cells.

6. The composition of claim 1, wherein the immortalized cells are Vero cells and the normal non-cancer cells are human dermal fibroblasts.

7. An intravenous composition comprising a non-replicating, cell internalizing Rhabdovirus-derived particle for treating leukemia in a subject in need thereof, wherein said Rhabdovirus-derived particle exhibits RNA which is cross-linked or cleaved into at least two discontinuous RNA polynucleotide sequences, wherein the composition is produced from a 50 µl sample of $1\times10^{10}$ plaque forming units per ml (PFU/ml) of live Rhabdovirus subjected to a UV dose of 250 mJ/cm$^2$ for about 40 seconds, the composition inducing less than 40% viability of immortalized Vero cells and about 80% viability of normal neonatal human dermal fibroblasts, in an in vitro cytotoxicity assay using a multiplicity of infection of 100 particles per cell and wherein the composition induces immunogenic apoptosis upon in-vivo administration to a subject.

* * * * *